US010561081B2

(12) United States Patent
Ozawa et al.

(10) Patent No.: US 10,561,081 B2
(45) Date of Patent: Feb. 18, 2020

(54) FERTIGATION SYSTEM, FERTIGATION CONTROL SERVER, SALTS ACCUMULATION DETERMINATION METHOD, AND SOIL EC SENSOR

(71) Applicants: Routrek Networks, Inc., Kawasaki-shi (JP); MEIJI UNIVERSITY, Chiyoda-ku (JP)

(72) Inventors: Kiyoshi Ozawa, Kawasaki (JP); Shunrokuro Fujiwara, Kawasaki (JP); Shinichi Sasaki, Kawasaki (JP); Eiji Kita, Kawasaki (JP); Hironao Tokitsu, Kawasaki (JP); Hiroshi Taketazu, Kawasaki (JP)

(73) Assignees: Routrek Networks, Inc., Kawasaki-shi (JP); MEIJI UNIVERSITY, Chiyoda-ku (JP)

( * ) Notice: Subject to any disclaimer, the term of this patent is extended or adjusted under 35 U.S.C. 154(b) by 129 days.

(21) Appl. No.: 15/561,402

(22) PCT Filed: Mar. 29, 2016

(86) PCT No.: PCT/JP2016/060203
§ 371 (c)(1),
(2) Date: Sep. 25, 2017

(87) PCT Pub. No.: WO2016/158987
PCT Pub. Date: Oct. 6, 2016

(65) Prior Publication Data
US 2018/0103596 A1    Apr. 19, 2018

(30) Foreign Application Priority Data

Mar. 31, 2015  (JP) .................................. 2015-072393

(51) Int. Cl.
*A01G 27/00*  (2006.01)
*A01G 7/06*  (2006.01)
(Continued)

(52) U.S. Cl.
CPC .......... *A01G 27/003* (2013.01); *A01C 23/007* (2013.01); *A01G 7/06* (2013.01); *A01G 27/008* (2013.01); *G01N 27/04* (2013.01)

(58) Field of Classification Search
CPC ........ A01G 25/00; A01G 25/16; A01G 27/00; A01G 27/003; A01G 27/008; A01G 29/00; A01G 7/06
(Continued)

(56) References Cited

U.S. PATENT DOCUMENTS 4,216,789 A * 8/1980 Hasenbeck .......... A01G 25/167
                                                    137/78.3
4,430,020 A * 2/1984 Robbins ................. A01G 25/02
                                                    405/43
(Continued)

FOREIGN PATENT DOCUMENTS

JP          10-10066 A     1/1998
JP       2000-125680 A     5/2000
(Continued)

OTHER PUBLICATIONS

Extended European Search Report dated Feb. 26, 2019 in the corresponding European Application No. 16772868.2 citing document AO therein 8 pages.
(Continued)

*Primary Examiner* — Kathleen I Alker
(74) *Attorney, Agent, or Firm* — Oblon, McClelland, Maier & Neustadt, L.L.P.

(57) ABSTRACT

A fertigation system comprises: a controller that transmits sensor data to a fertigation control server, and that controls
(Continued)

a water supply valve, a culture stock solution supply valve, and a discharge valve on the basis of received data; and a fertigation control server that, on the basis of the sensor data received from the controller, calculates control amounts for the water supply valve, the culture stock solution supply valve, and the discharge valve, and returns the control amounts to the controller.

6 Claims, 23 Drawing Sheets

(51) Int. Cl.
    *G01N 27/04*     (2006.01)
    *A01C 23/00*     (2006.01)
(58) Field of Classification Search
    USPC .................................................. 47/48.5, 57.5
    See application file for complete search history.

(56) References Cited

U.S. PATENT DOCUMENTS

| | | | | |
|---|---|---|---|---|
| 7,809,475 | B2* | 10/2010 | Kaprielian | A01C 23/042 137/78.3 |
| 8,924,031 | B1* | 12/2014 | Evett | A01G 25/16 700/284 |
| 9,538,714 | B2* | 1/2017 | Anderson | A01G 25/167 |
| 9,943,046 | B2* | 4/2018 | Bermudez Rodriguez | A01G 25/092 |
| 2002/0167412 | A1* | 11/2002 | Cuming | A01G 25/167 340/602 |
| 2008/0288116 | A1* | 11/2008 | Nickerson | A01G 25/16 700/284 |
| 2011/0219686 | A1* | 9/2011 | Heide | A01N 43/50 47/58.1 R |
| 2012/0095604 | A1* | 4/2012 | Alexanian | A01G 25/16 700/284 |
| 2012/0290140 | A1* | 11/2012 | Groeneveld | A01G 22/00 700/284 |
| 2014/0236868 | A1* | 8/2014 | Cook | A01G 25/16 705/412 |
| 2015/0032272 | A1* | 1/2015 | Neesen | A01G 25/16 700/284 |
| 2016/0143228 | A1* | 5/2016 | De Groot | A01G 9/24 700/284 |
| 2018/0242539 | A1* | 8/2018 | Bhattacharya | A01G 7/045 |

FOREIGN PATENT DOCUMENTS

| | | |
|---|---|---|
| JP | 2003-79215 A | 3/2003 |
| JP | 2005-164436 A | 6/2005 |
| JP | 2009-100703 A | 5/2009 |
| JP | 2010-166871 A | 8/2010 |
| JP | 2012-147753 A | 8/2012 |

OTHER PUBLICATIONS

International Search Report dated Jul. 5, 2016 in PCT/JP2016/060203 (submitting English translation only) citing documents AO-AT, therein 4 pages.

* cited by examiner

OPERATION OF CONTROLLER

CULTURE SOLUTION AMOUNT AND CONCENTRATION CALCULATION PROCESS BY FERTIGATION CONTROL SERVER

DISCHARGE VALVE NUMBER: #1
GREENHOUSE NUMBER: #1
CROP BEING CULTIVATED: CUCUMBER

HARVEST COMPLETED?

| YES | NO | RETURN |

DISCHARGE VALVE NUMBER: #1
GREENHOUSE NUMBER: #1
CROP BEING CULTIVATED: NONE
SENSOR NUMBER: #1

[SALTS ACCUMULATION DETERMINATION ENABLED]
DO YOU WANT TO PERFORM SALTS
ACCUMULATION DETERMINATION?

| YES | NO | RETURN |

FIG. 21B

SALTS ACCUMULATION DETERMINATION BEING PERFORMED
GREENHOUSE NUMBER: #1
SENSOR NUMBER: INJECT GLUCOSE INTO EC SENSOR #1

GLUCOSE INJECTION COMPLETED?

| YES | NO | RETURN |

FIG. 21C

FERTIGATION SYSTEM, FERTIGATION CONTROL SERVER, SALTS ACCUMULATION DETERMINATION METHOD, AND SOIL EC SENSOR

TECHNICAL FIELD

The present invention relates to a fertigation system, a fertigation control server used for the fertigation system, a salts accumulation determination method for determining salts accumulation of soil for soil cultivation, and a soil EC sensor suitable for the salts accumulation determination method.

Note that, the "crops" mentioned in the present description include agricultural crops and foliage plants.

BACKGROUND ART

In our country, Japan, with its small land area, enhancing the efficiency and increasing the profitability of agriculture are an urgent problem to be solved.

The inventors have been studying fertigation as a promising method to enhance the efficiency and profitability of agriculture, and working on development of a system expected to highly realize the same.

Fertigation is a water-saving crop cultivation technique, which provides culture solution prepared by diluting fertilizer with an appropriate amount of water to crops being cultivated in soil by a required amount at a required time using an irrigation tube.

Patent Literature 1 is a prior art literature of a cultivation method of crops using fertigation, which seems to be partially related to the present invention. Patent Literature 1 has disclosed a method of cultivating crops by fertigation, the method including: (1) a unit configured to analyze soil and measure chlorine ion density and sulfate ion density in the soil, prior to cultivating crops; (2) a unit configured to acquire a contribution value (ds/m) of chlorine ions and sulfate ions to electrical conductivity; (3) a unit configured to determine a management target value for the electrical conductivity of soil solution by adding the contribution value acquired at above (2) to a standard electrical conductivity; (4) a unit configured to measure the electrical conductivity in the soil solution during a cultivation period; and (5) a unit configured to adjust the density and the amount of fertilization solution to be supplied when performing fertilization so that the electrical conductivity acquired at above (4) is maintained within the range of the management target value determined at above (3).

CITATION LIST

Patent Literature

PTL 1: Japanese Patent Laid-Open No. 2003-79215

SUMMARY OF INVENTION

Technical Problem

Prior art fertigation is classified into a simplified system using a timer, and a computer-controlled system.

In the case of the former, which is not capable of taking a quick action against the change of weather, there has been a concern of over-fertilization which may lead to pollution of groundwater.

In the case of the latter, introduction of a computer system requires a large amount of funds.

It is an object of the present invention to solve the above-described problems, by providing a fertigation system which can be easily introduced by a personal enterprise and also can realize a high-level control, a fertigation control server, a salts accumulation determination method, and a soil EC sensor to be used therefor.

Solution to Problem

In order to solve the above-described problems, a fertigation system of the present invention includes: a discharge valve configured to receive supply of culture solution from a culture solution preparing section that supplies the culture solution prepared by mixing water and culture stock solution, and control supply and interruption of the culture solution to soil where a crop is cultivated; a first irrigation tube configured to spray the culture solution on the soil, upon receiving supply of the culture solution from the discharge valve; a second irrigation tube configured to spray the culture solution on the soil, upon receiving supply of the culture solution from the discharge valve, together with the first irrigation tube; a controller configured to control, on a basis of predetermined control information, preparation of the culture solution by the culture solution preparing section and opening and closing of the discharge valve. A control data generating section calculates an opening time of the discharge valve by the culture solution preparing section, on a basis of length of the first irrigation tube, length of the second irrigation tube, and culture solution supply capacity per unit time of the discharge valve, and provides the controller with the control information including the opening time of the discharge valve.

Advantageous Effects of Invention

According to the present invention, it is possible to provide a fertigation system which can be easily introduced by a personal enterprise and also can realize a high-level control, a fertigation control server, a salts accumulation determination method, and a soil EC sensor to be used therefor.

Problems, configurations, and effects other than those mentioned above will be apparent from the following description of embodiments.

BRIEF DESCRIPTION OF DRAWINGS

FIGS. 21A, 21B and 21C are display screens of a terminal in accordance with a salts accumulation determination function;

DESCRIPTION OF EMBODIMENTS

Figure 1A:
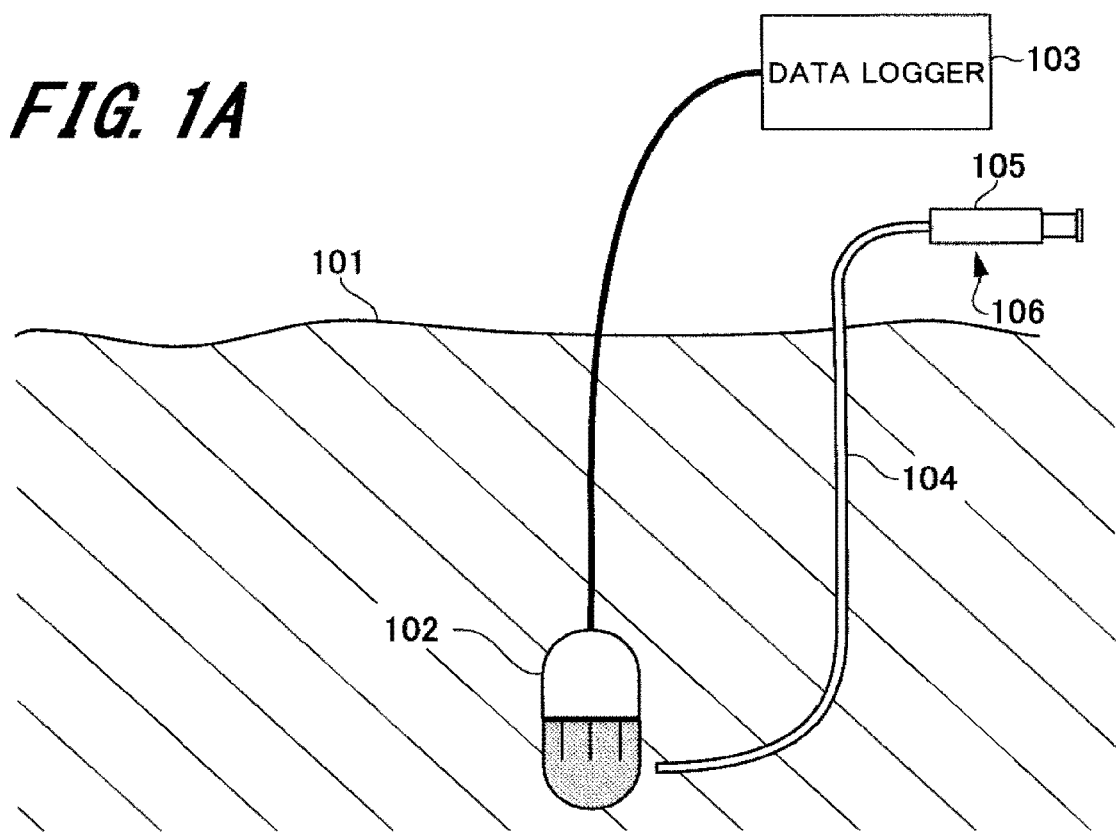
FIG. 1A is a schematic diagram describing a first salts accumulation determination method.

Soil cultivation is classified into open cultivation and greenhouse cultivation, that is, cultivation in a vinyl house or a greenhouse. For soil cultivation in Japan, the greenhouse cultivation is widely performed, which is easy to mitigate climate variation and control the growth environment of crops. Penetration rate of the greenhouse cultivation is particularly high in cold districts, such as Tohoku area and Hokkaido area. Note that, hereafter, the vinyl house and the greenhouse will be collectively referred to as a "greenhouse".

The greenhouse cultivation in Japan is suffering from salts accumulation in about 80% of the soil, and it has been proven to be the cause of decreased productivity of the greenhouse cultivation. Salts accumulation refers to a phenomenon in which the concentration of nitrate ions ($NO_3^-$: nitrate-nitrogen) in the soil has become substantially higher than an appropriate value due to over-fertilization of the soil, thereby exerting adverse influence on the growth of crops.

Soil EC sensors currently available in the market for measuring the concentration of nitrate-nitrogen in the soil have a problem which is very difficult to solve such that the absolute value of the acquired measurement value is untrustworthy due to the fact that the target of measurement exists in the soil. Accordingly, determination of salts accumulation in the soil turns out to be extensive in that it requires preliminary collection of soil, use of a dedicated measurement device, and the like, and also requires a large cost.

For a farming family working on the greenhouse cultivation, a specific value of salts accumulated in the soil is not important, but rather whether or not the soil is in a salt-accumulated state is important. Therefore, provision of a simple and inexpensive method for determining salts accumulation in the soil is desired.

It is an object of the present invention to solve the above-described problems, by providing a salts accumulation determination method which can be easily performed by a personal enterprise, a soil EC sensor suitable for the salts accumulation determination method, a fertigation system, and a fertigation control server to be used for the fertigation system.

In the following description of embodiments, two methods for determining salts accumulation will be first described. The first one is an extremely simplified salts accumulation determination method. The second one is a more accurate salts accumulation determination method considering the existence of a plurality of types of salts in the soil.

Next, a new soil EC sensor in accordance with the determination method of salts accumulation will be described.

It is conceivable to use a function of a fertigation system using computer control, as a system for performing the second salts accumulation determination method. Accordingly, a fertigation system under study and development by the inventors will be described first. Subsequently, an embodiment will be described in which a fertigation system, having grasped that the soil to be determined is in a state where crops are not cultivated by a log function of the fertigation system, performs a salts accumulation determination process.

[First Salts Accumulation Determination Method]

Figure 1B:
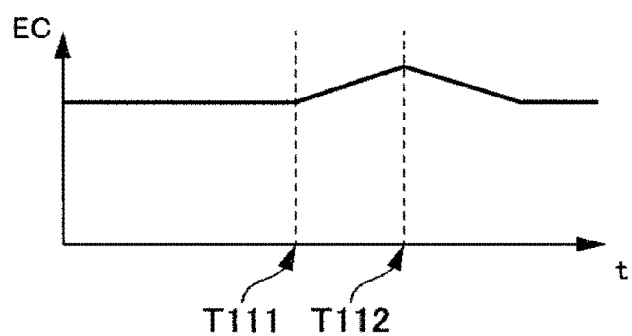
FIGS. 1B and 1C are schematic graphs illustrating the variation of the EC value in normal soil without salts accumulation and that in soil with occurrence of salts accumulation, respectively.
Figure 1C:
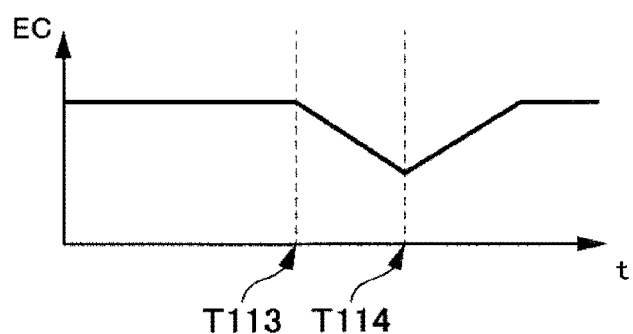

FIG. 1A is a schematic diagram illustrating a first salts accumulation determination method according to the present invention. FIG. 1B is a schematic graph illustrating the variation of the EC value in normal soil without salts accumulation. FIG. 1C is a schematic graph illustrating the variation of the EC value in soil with occurrence of salts accumulation. Note that, although actual variation of the EC value is a curve accompanied with fluctuation, the variation of the EC value is intentionally represented by a line graph using straight lines in FIGS. 1B and 1C for ease of understanding. Further, the same goes for FIGS. 3, 22, and 23 described below.

When performing soil cultivation for any type of crop, a soil EC sensor (hereinafter abbreviated as "EC sensor") 102 is first buried into soil as deep as about 30 to 50 cm from the ground surface of soil 101, prior to cultivation of the crops, in order to check whether or not salts accumulation has occurred in the soil 101 in which soil cultivation is performed. EC, an abbreviation for "Electrical Conductivity", refers to the electrical conductivity in the soil indicating the content of nitrate-nitrogen. In other words, EC in turn is treated as information approximately synonymous with the concentration of the fertilizer in the soil. The depth of burial of the EC sensor 102 is desired to be a depth adapted to the length of the root growing out of the crops when the crops are growing. Burying the EC sensor 102 too close to the ground surface may obstruct measurement of the EC value because soil water easily evaporates.

The EC sensor 102 is connected to a data logger 103. The data logger 103 causes a predetermined amount of weak alternating current to flow through the EC sensor 102, and measures an EC value.

Reference culture solution 106 is injected with a syringe 105, via a tube 104 or the like, into the vicinity of the EC sensor 102 which has started measuring EC value using the data logger 103. The reference culture solution 106 is a type of culture solution with only nitrate-nitrogen being adjusted to a predetermined concentration as anions associated with the EC value for use in fertigation or the like. For example, the concentration of nitrate-nitrogen is 120 ppm. This concentration corresponds to culture solution with a standard concentration for use in normal soil cultivation or the like.

Injection of the reference culture solution 106 into the vicinity of the EC sensor 102 exhibits a change in the trend of the variation of the EC value depending on whether or not the soil 101 having the reference culture solution 106 injected therein has caused salts accumulation.

In the case of normal soil without salts accumulation, the EC value is lower than that of the reference culture solution 106 injected with the syringe 105. Therefore, as illustrated in FIG. 1B, the EC value rises (T112) after a period of about one to several hours has passed from the time point (T111) when the reference culture solution 106 was injected. Subsequently, after having reached an extreme value at a certain time point, the EC value returns to its original value. Note that the extreme value is approximately equal to the EC value of the reference culture solution 106.

In the case of soil with occurrence of salts accumulation, the EC value is higher than that of the reference culture solution 106 injected with the syringe 105. Therefore, as illustrated in FIG. 1C, the EC value drops (T114) after a period of about one to several hours has passed from the time point (T113) when the reference culture solution 106 was injected. Subsequently, after having reached an extreme value at a certain time point, the EC value returns to its original value. Note that the extreme value is approximately equal to the EC value of the reference culture solution 106.

As thus described, injection of the reference culture solution 106 to the vicinity of the EC sensor 102 allows for determining salts accumulation in about several hours.

As is known in the art, soil has buffering ability. Although performing fertilization and irrigation locally on a certain single location of soil results in a temporary rise in the amount of the fertilization and the amount of water in the single location, ingredient and water of the fertilizer disperses from the single location to its periphery in the course of time and returns to a condition close to the original value before performing fertilization and irrigation. In addition, the variation of the amount of fertilization and the amount of water is very slow.

[Second Salts Accumulation Determination Method]

The inventors have experimented determination of salts accumulation in various types of soil, using the above-described first salts accumulation determination method. It has been revealed through collection of data that there are cases where the first salts accumulation determination method is not capable of accurately determining salts accumulation. Further, it has also been revealed that the cause thereof is that, when measuring the EC value in the soil with the EC sensor 102, anions involved in the EC value include not only nitrate ions but also chlorine ions ($Cl^-$) and sulfate ions ($SO_4^{2-}$).

Chlorine ions and sulfate ions do not nourish crops but rather obstructive for the growth of crops. Therefore, grasping the amount of chlorine ions and sulfate ions included in the soil allows for determining salts accumulation more accurately.

Accordingly, a salts accumulation determination method which is more accurate than the first salts accumulation determination method will be described in the following.

Figure 2A:
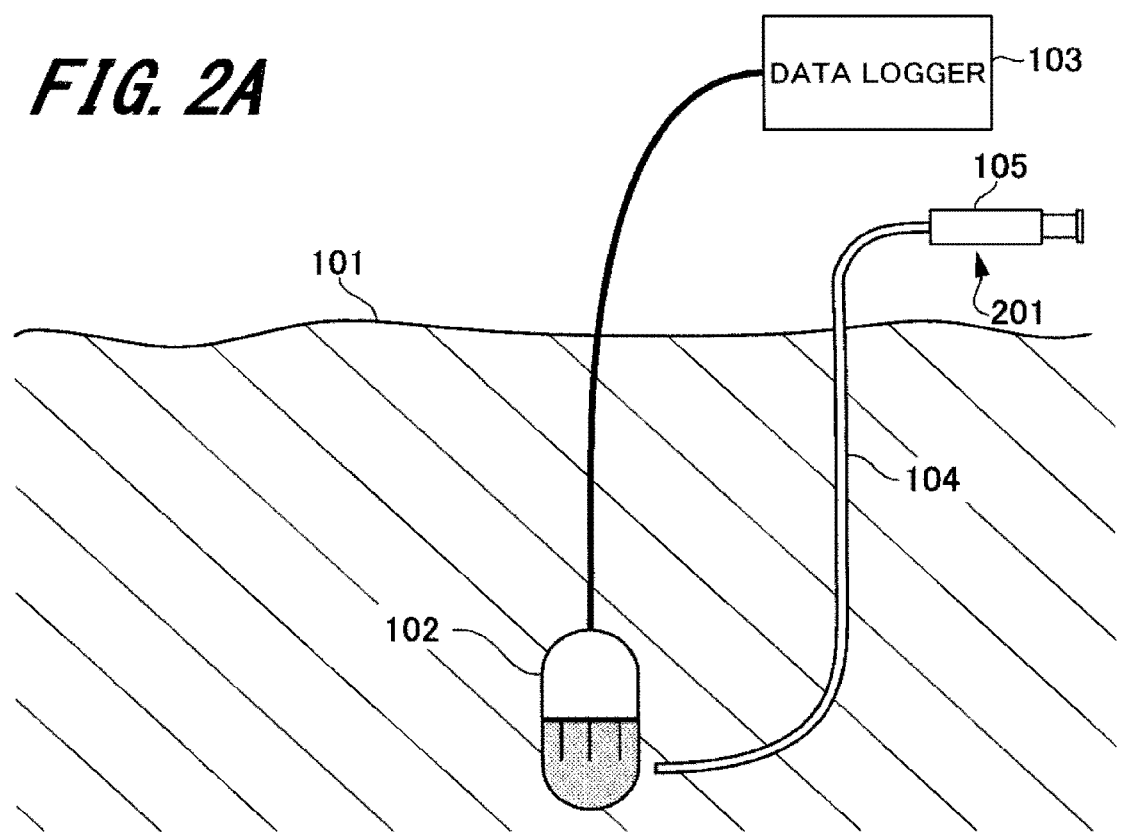
FIGS. 2A and 2B are schematic diagrams illustrating a first procedure and a fourth procedure of a second salts accumulation determination method, respectively.
Figure 2B:
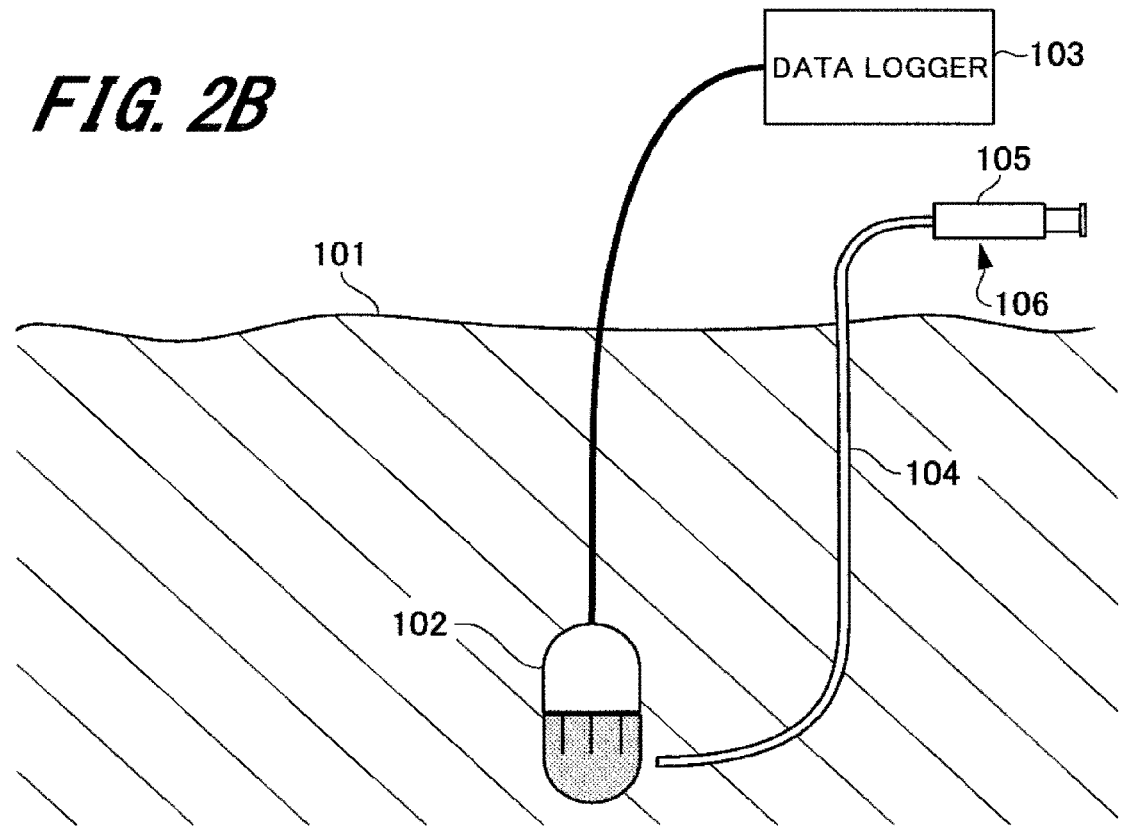
Figure 3A:
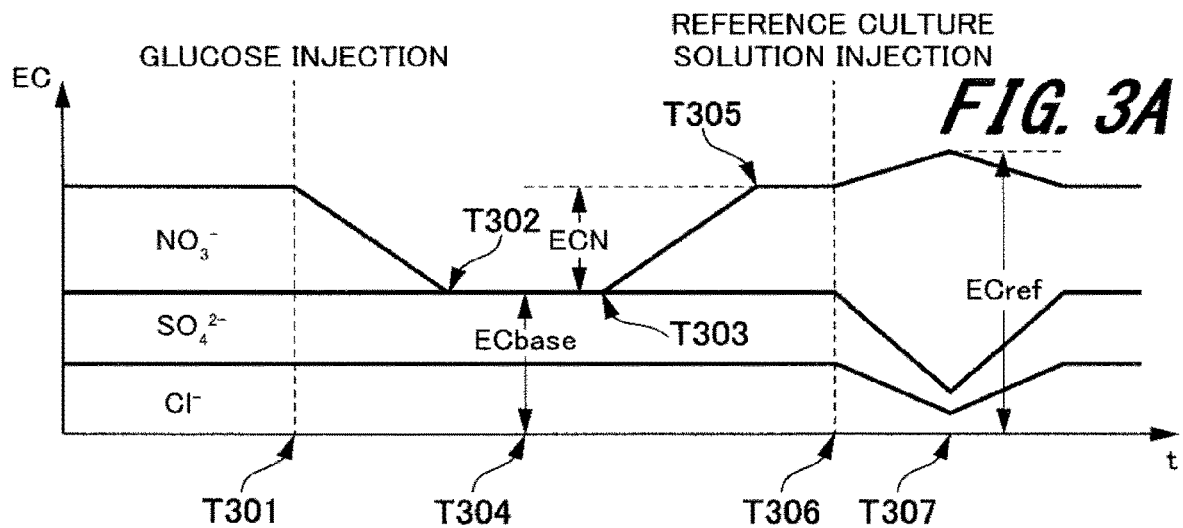
FIGS. 3A and 3B are schematic graphs illustrating the variation of the EC value in normal soil of a first type and a second type without salts accumulation, respectively.
Figure 3B:
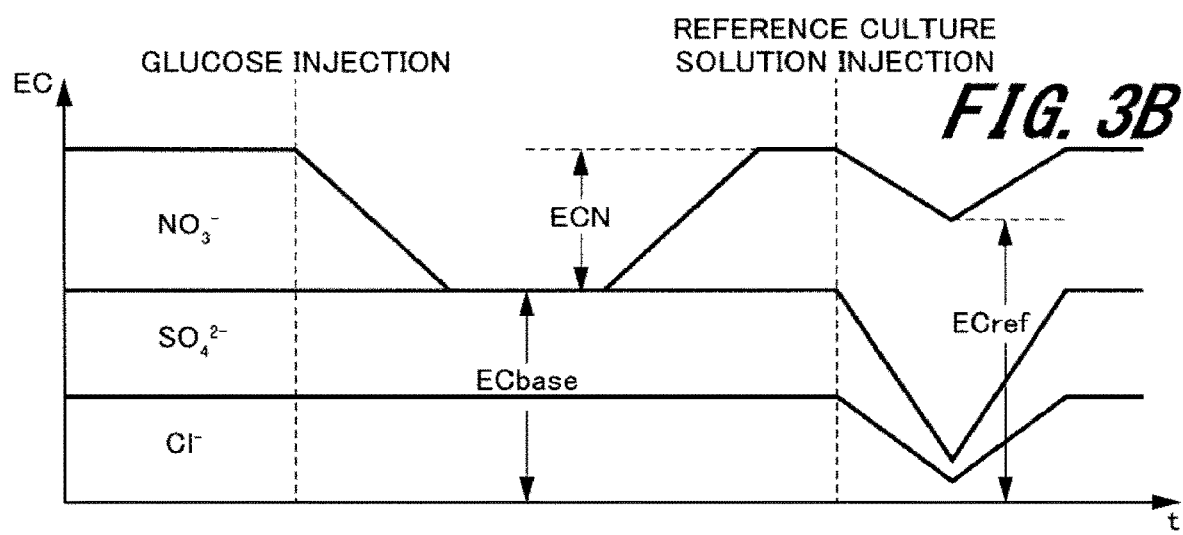
Figure 3C:
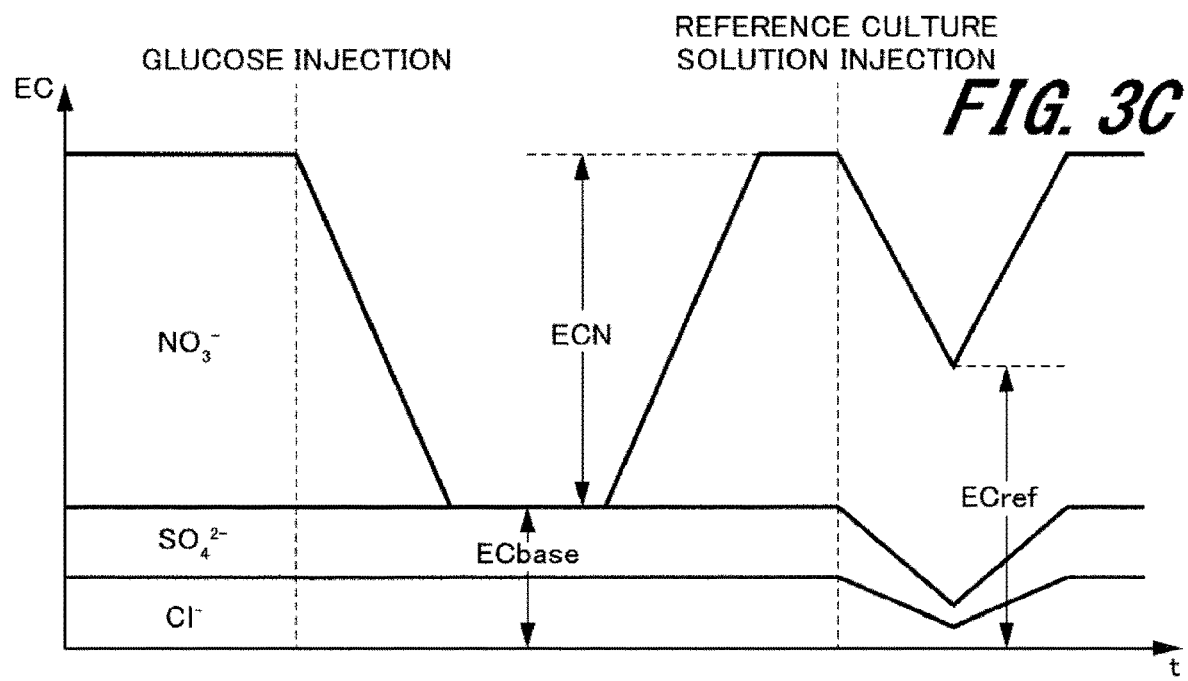
FIG. 3C is a schematic graph indicating the variation of the EC value in soil with occurrence of salts accumulation.

FIG. 2A is a schematic diagram illustrating a first procedure of a second salts accumulation determination method according to the present invention. FIG. 2B is a schematic diagram illustrating a fourth procedure of the second salts accumulation determination method according to the present invention. FIG. 3A is a schematic graph illustrating the variation of the EC value in normal soil of a first type without salts accumulation. FIG. 3B is a schematic graph illustrating the variation of the EC value in normal soil of a second type without salts accumulation. FIG. 3C is a schematic graph illustrating the variation of the EC value in soil with occurrence of salts accumulation.

First, a procedure of the second salts accumulation determination method will be described below.

First procedure: As illustrated in FIG. 2A, carbohydrate aqueous solution, such as glucose (grape sugar) 201, is injected into the vicinity of the EC sensor 102.

Second procedure: As illustrated in FIG. 3A, the EC value at the time point when the value of the EC sensor 102 has reached the bottom is measured and acquired as "ECbase".

Third procedure: As illustrated in FIG. 3A, the value of the EC sensor 102 at the time point when the value of the EC sensor 102 has risen again is measured and acquired.

Fourth procedure: As illustrated in FIG. 2A, after acquisition of the value of the EC sensor 102, the reference culture solution 106 is injected into the vicinity of the EC sensor 102.

Fifth procedure: As illustrated in FIGS. 3A, 3B, and 3C, upon checking that the value of the EC sensor 102 has risen or dropped and then returned to its original value again, the EC value is acquired at the time point of indicating an extreme value.

Note that, measurement of the EC value is continuously performed, for example, every 10 minutes in the course of the first to the fifth procedures.

As thus described, there may also exist, in the soil, chlorine ions and sulfate ions which do not nourish crops besides nitrate ions which nourish crops. A high concentration of chlorine ions and sulfate ions may cause the EC value to drop after reference culture solution injection as illustrated in FIG. 1C, even when the concentration of nitrate ions is low. Therefore, it is necessary to preliminarily grasp the concentration of chlorine ions and sulfate ions other than nitrate ions, among the anions in the soil. With regard to the measurement of the EC value, however, it is impossible to perform a measurement such as separately measuring for different types of anions.

The inventors, therefore, have considered grasping the concentration of chlorine ions and sulfate ions other than nitrate ions among the anions in the soil by removing nitrate ions from the soil. In order to remove nitrate ions from the soil, it suffices to convert nitrate ions into materials which are not nitrate ions. To do so, it is effective to cause bacteria in the soil to consume nitrate-nitrogen included in nitrate ions so that the nitrate-nitrogen taken in by the bacteria is converted into organic nitrogen.

As for bacteria, those capable of causing nitrogen starvation in the soil are preferable. For example, general bacteria existing in the soil in a huge number, such as pseudomonas or bacillus, consume nitrate-nitrogen included in nitrate ions when the bacteria proliferate. For that matter, however, it is necessary to supply the soil with a large amount of carbohydrates, such as glucose 201, which nourish bacteria. It is preferable that for causing bacteria to consume nitrate-nitrogen, the mass ratio (C/N ratio) of carbon relative to nitrate-nitrogen is 10 or more.

Accordingly, in the first procedure, carbohydrate aqueous solution, such as glucose 201, is first injected into the vicinity of the EC sensor 102 by an amount of about 50 cc, for example, as illustrated in FIG. 2A. This event corresponds to a time point T301 of FIG. 3A. Subsequently, bacteria in the soil consume carbohydrates together with nitrate-nitrogen included in nitrate ions, whereby the nitrate ion concentration decreases. In the course of time, the nitrate ion concentration becomes almost zero in the soil in the vicinity of the EC sensor 102, and the EC value drops as low as a certain value. This event corresponds to a time point T302 of FIG. 3A. This state is kept until the carbohydrates included in carbohydrate aqueous solution injected with the syringe 105 into the soil are almost completely consumed by bacteria. This event corresponds to a time point T303 of FIG. 3A.

As thus described, the state in which the EC value exhibits little variation continues for a certain period from the time point T302 to a time point T303. In the second procedure, therefore, the EC value at this time point is measured and held. Hereafter, the EC value at the time point T304 will be referred to as "ECbase". ECbase is an EC value in the soil including almost no nitrate ions, and is approximately equal to the concentration of chlorine ions and sulfate ions in the soil.

When carbohydrates in the carbohydrate aqueous solution injected with the syringe 105 into the soil have been consumed by bacteria, nitrate ions seep out from the soil around the EC sensor 102. The EC value then rises again. Finally, the EC value returns to a value close to the EC value at the time point of injecting the carbohydrate aqueous solution. This event corresponds to a time point T305 of FIG. 3A. After the time point T305, the EC value turns into equilibrium. This event continues from the time point T305 to T306.

Accordingly, in the third procedure, an EC value is acquired at the time point T306 when the EC value has reached equilibrium after having risen again at the time point T305. ECt, which is the EC value at this time point is expressed by the following Formula 1.

$$ECt = ECN + ECbase \quad \text{(Formula 1)}$$

where ECN:EC value of nitrate ions in the soil

Next, in the fourth procedure, the reference culture solution 106 is injected into the vicinity of the EC sensor 102. This event corresponds to the time point T306 of FIG. 3A. The EC value then varies due to the reference culture solution 106. Subsequently, after the EC value has reached an extreme value at a time point T307 of FIG. 3A, the EC value gradually approaches the state at the original time point T306 due to the buffering ability of the soil. In the fifth procedure, therefore, the EC value at the time point T307 is acquired. "ECref" in FIGS. 3A, 3B, and 3C is the EC value at the time point T307. Whether or not the current time has reached the time point T307 is determined by continuous measurement of the EC value such that the time point T307 has been reached when the direction of variation of EC value has reversed.

The discriminant formula for determining salts accumulation is as follows. When the following inequality holds, salts accumulation has not occurred in the soil.

$$(ECN + ECbase) - ECref \leq ECbase \quad \text{(Formula 2)}$$

Formula 2 represents that the variation of the EC value before and after injection of the reference culture solution 106 determines whether or not ECbase is exceeded.

Referring to FIGS. 3A, 3B, and 3C again, the trend of the variation of the EC value and the determination method of salts accumulation will be described. Here, FIGS. 3A, 3B, and 3C are illustrated as though chlorine ions and sulfate ions after injection of reference culture solution affect ECref, which is the EC value, for the purpose of explaining the general idea. Actually, however, injection of reference culture solution causes significant drop of the ion concentration and therefore chlorine ions and sulfate ions have little influence on ECref. Accordingly, ECref is substantially equal to the EC value of the reference culture solution 106.

FIG. 3A is a schematic graph illustrating the variation of the EC value in normal soil without salts accumulation. The soil according to FIG. 3A is equivalent to that of FIG. 1B in the first salts accumulation determination method. As can be seen, the EC value rises before and after injecting the reference culture solution 106 into the vicinity of the EC sensor 102. In other words, the left side of the above-described Formula 2 turns out to be a negative value. Therefore, with the condition of Formula 2 being satisfied, it can be determined that there is no salts accumulation.

FIG. 3B is a schematic graph illustrating the variation of the EC value in normal soil without salts accumulation. The soil according to FIG. 3B has a larger ECbase than the soil of FIG. 3A. Accordingly, the EC value drops before and after injecting the reference culture solution 106 into the vicinity of the EC sensor 102 (from time point T306 to T307). Now, Formula 2 is verified. Then, it can be seen that the value acquired by subtracting ECref indicating the EC value at the time point T307 from the EC value ECt at the time point T306 is smaller than ECbase. Therefore, with the condition of Formula 2 being satisfied, it can be determined that there is no salts accumulation.

FIG. 3C is a schematic graph illustrating the variation of the EC value in soil with occurrence of salts accumulation. The soil according to FIG. 3C has a larger ECbase than the soil of FIG. 3A. Accordingly, the EC value drops before and after injecting the reference culture solution 106 into the vicinity of the EC sensor 102. Now, Formula 2 is verified. Then, it can be seen that the value acquired by subtracting ECref indicating the EC value at the time point T307 from the EC value ECt at the time point T306 is larger than ECbase. Therefore, since the condition of Formula 2 is not satisfied, it can be determined that salts accumulation has occurred.

Referring to Formula 2 again, ECbase appears in both sides of Formula 2. In other words, Formula 2 is $$ECN - ECref \leq 0 \quad \text{(Formula 3)}$$

and therefore can be rewritten into $$ECN \leq ECref \quad \text{(Formula 4)}.$$

In other words, the basis for determining whether or not salts accumulation has occurred is that the concentration of nitrate ions in the soil is equal to or lower than the concentration of nitrate ions of the reference culture solution 106.

Since it is difficult to acquire an accurate value of ECN for the calculation, ECbase is measured.

Note that, in FIGS. 3A, 3B, and 3C, ECref at the time point T307 includes not only nitrate ions but also a small amount of chlorine ions and sulfate ions. It is conceivable that the ions have been diluted by the reference culture solution 106.

The above-described case where the first salts accumulation determination method cannot accurately determine salts accumulation corresponds to the soil in the state of FIG. 3B. In other words, the soil is in a state such that, although salts accumulation seems to have occurred according to the EC value, the concentration of nitrate ions in the soil is not necessarily high. Performing cultivation on such soil with a reduced amount of fertilization leads to insufficient supply of nitrate ions required for the growth of crops, preventing the crops from growing normally. The second salts accumulation determination method correctly determines the soil in the state of FIG. 3B.

As thus described, injecting carbohydrate aqueous solution, such as glucose 201, into the vicinity of the EC sensor 102 and injecting the reference culture solution 106 after having reduced nitrate ions can realize more accurate determination of salts accumulation.

[EC Sensor 401]

Today, EC sensors available in the market are expensive. For farming families, most of which are personal enterprises, purchasing a large number of EC sensors is economically a large burden.

In addition, the values measured by an EC sensor may easily vary depending on the state of installation in the soil, the force applied to the soil and the EC sensor, the amount of water in the soil, or the like, and therefore the absolute values of the measurements are untrustworthy. Accordingly, when using an EC sensor to control soil cultivation, the EC sensor should be referred to for calculating the amount of fertilization in view of the increase or decrease, i.e., the relative variation of the value.

The EC value in the soil varies slowly due to the buffering ability of the soil. Further, an EC sensor should be referred to in terms of the amount of relative variation only, and not the absolute value thereof. Taking this idea into account in conjunction with the above-described second salts accumulation determination method, it becomes very easy to realize an EC sensor.

The inventors have come up with a very simple EC sensor by isolating the sensor module of the EC sensor from the soil which is the variation factor of the EC value to be measured.

Figure 4A:
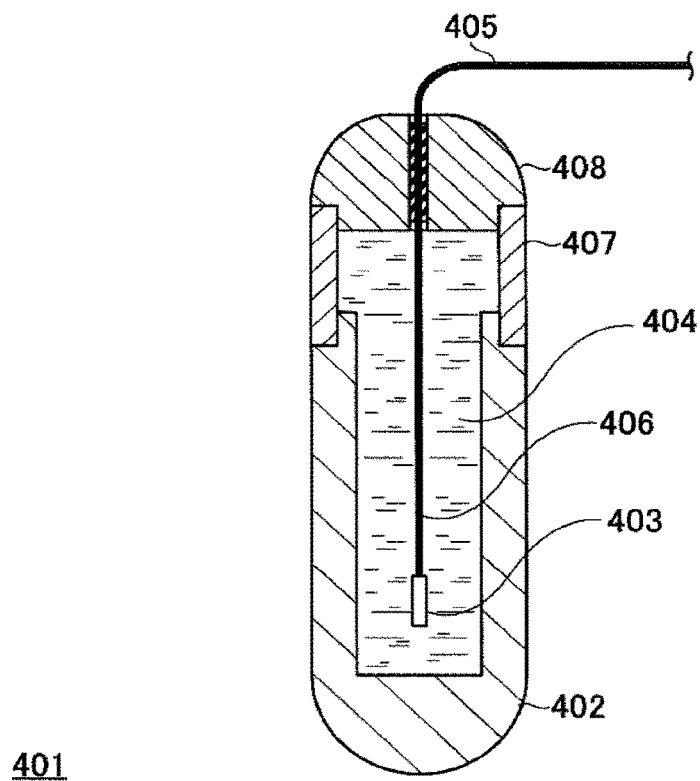
FIG. 4A is a cross-sectional view of an EC sensor according to the present embodiment.
Figure 4B:
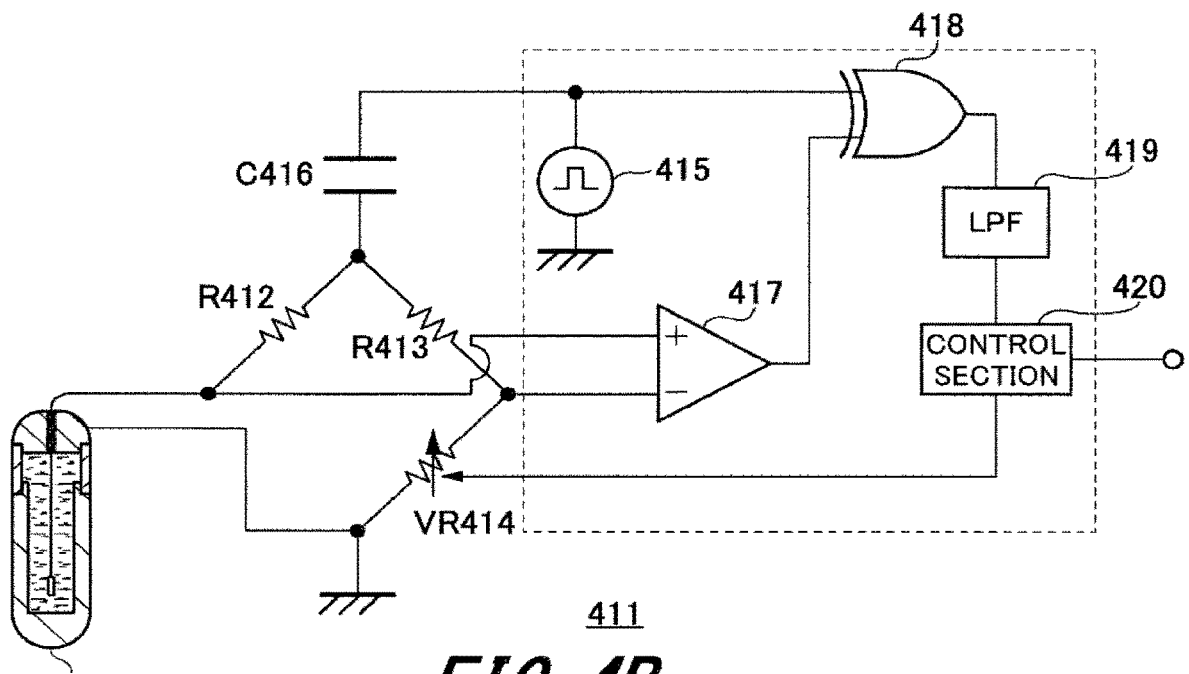
FIG. 4B is a block diagram of a simplified EC value measurement device using an EC sensor.

FIG. 4A is a cross-sectional view of an EC sensor 401 according to the present embodiment. FIG. 4B is a block diagram of a simplified EC value measurement device 411 using the EC sensor 401. First, referring to FIG. 4A, the structure of the EC sensor 401 will be described.

The EC sensor 401 has a structure in which an electrode 403 and water are sealed in a publicly known porous cup 402. The porous cup 402, having the full length of about 10 cm, has a core wire 406 of a coaxial cable 405 extending downward, with the electrode 403 made of corrosion-proof metal, such as gold or stainless steel, being provided on the tip of the core wire 406. An aperture portion of the top surface of the porous cup 402 has connected thereto a pipe 407 made of an insulator, such as vinyl chloride, and the pipe 407 further has mounted thereon a cap 408 made of corrosion-proof metal, such as gold or stainless steel. The center of the cap 408 has a hole perforated therein, and the hole has the coaxial cable 405 inserted therein together with a rubber packing. The coated wire of the coaxial cable 405, i.e., a cable ground (ground electrode) is in contact with the cap 408 and therefore the cap 408 is connected to the cable ground. In other words, it can be said that the ground electrode is provided on the cap 408 that seals water from the porous cup 402.

When the EC value is measured, electric current flows in the water filled in the porous cup 402 existing between the electrode 403 and the cable ground.

When the EC sensor 401 is installed in the soil, the porous cup 402 is preliminarily filled with pure water. Subsequently the EC sensor 401 is buried in the soil.

Since the porous cup 402 is an unglazed container, anions in the soil will seep into pure water in the porous cup 402 of the EC sensor 401 buried in the soil, through innumerable minute holes formed in the porous cup 402. Then, in the course of time, the anion concentration in the water in the porous cup 402 and the anion concentration in the soil turn into equilibrium. Provided that the soil is not dry, the water in the porous cup 402 never dries up.

The EC sensor 401 having the above-described configuration has an outstanding advantage of being very stable against vibration, impact, pressure, or the like, on the soil, which has been unseen in the conventional EC sensor 401. With the EC value of water in the EC sensor 401 being the target to be directly measured, the electrode 403 of the EC sensor 401 is isolated from uncertainties existing in the soil, whereby a stable measurement of the EC value can be realized.

On the other hand, the EC sensor 401 described above is not capable of immediately measuring the variation of the EC value in the soil. However, in the first place, the anion concentration in the soil varies slowly, and therefore the anion concentration in the water inside the EC sensor 401 can follow the variation of the anion concentration in the soil with the approximately same speed. Therefore, the above-described shortcoming will be of no problem at the actual operation.

Furthermore, although the porous cup 402, having been made in general for absorbing water in the soil by applying negative pressure thereon, is supposed to be disposable in conventional use, the EC sensor 401 of the present embodiment does not apply negative pressure on the porous cup 402. Therefore, with no clogging of the minute holes of the porous cup 402, the life of the porous cup 402 is very long. The porous cup 402 currently available in the market is in itself made for disposable use and therefore very inexpensive. In other words, the EC sensor 401 of the present embodiment may be realized in a very inexpensive manner.

Referring to FIG. 4B, an example of the simplified EC value measurement device 411 using the EC sensor 401 of the present embodiment will be described.

When the electrical conductivity of liquid or the like is measured, it is necessary to cause an alternating current to flow through the sensor, in order to prevent polarization on the surface of an electrode included in the sensor. Measurement of the EC value with the EC sensor 401, being no exception, may be realized by causing a weak alternating current to flow through the EC sensor 401 and detecting the current.

In FIG. 4B, resistors R412 and R413, a variable resistor VR414, and the EC sensor 401 form a publicly known Wheatstone bridge. The EC sensor 401 is equivalent to a resistor on one side of the publicly known Wheatstone bridge. One end of the variable resistor VR414 and the cable ground of the EC sensor 401 are connected to the ground node.

The variable resistor VR414, being a digital potentiometer, can provide a control value to set a resistor value.

An output signal of a square wave voltage source 415 has its direct current offset component removed by a capacitor C416, and an alternating signal flows from a connection point of the resistors R412 and R413. Intersection terminals of the bridge are respectively input to a comparator 417. Since an alternating signal flows in the bridge, alternating current is also output to the comparator 417. However, the phase of the square wave alternating signal output from the comparator 417 changes by 180°, depending on which of the electric potential of the EC sensor 401 and the electric potential of the variable resistor VR414 is higher.

Output signals from the comparator 417 are input to an Exclusive-OR gate (hereinafter, "EXOR" gate) 418. On the other hand, output signals from the square wave voltage source 415 are also input to the EXOR gate 418. An output logic signal from the EXOR gate 418 turns logically true or false, according to whether input signals are of a same logic value or different logic values, i.e., whether they are in phase or reversed by 180°. Since an output signal from the EXOR gate 418 may include noise, removing the noise from the output signal using an LPF 419 or the like allows for acquiring a logic signal indicating which of the impedance of the EC sensor 401 and the impedance of the variable resistor VR414 is higher.

A control section 420, upon acquiring the logic signal, varies the impedance of the variable resistor VR414. Control of the impedance is performed using, for example, a publicly known binary search method.

The square wave voltage source 415, the comparator 417, the EXOR gate 418, the LPF 419, and the control section 420 located within the dotted line frame may be realized by an inexpensive one-chip microcomputer. There is a one-chip microcomputer incorporating a comparator, and thus the comparator may be directly used. In other words, the simplified EC value measurement device 411 may be realized by two resistors, a capacitor, a digital potentiometer, and a one-chip microcomputer.

The simplified EC value measurement device 411 illustrated in FIG. 4B does not require any adjustment process after manufacturing of the device since it suffices to appropriately select the resistor of the bridge provided that the upper limit and the lower limit of impedance reachable by the EC sensor 401 are preliminarily known. For example, although a measurement device using an A/D converter requires a process of adjusting output values from the A/D converter, the simplified EC value measurement device 411 illustrated in FIG. 4B, which does not require any such adjustment process, exhibits a high reproducibility.

The reference value of the EC sensor 401 can be used for calibrating the EC sensor 401 by injecting the reference culture solution 106 into the vicinity of the EC sensor 401.

When it is apparent that salts accumulation has not occurred in the soil, the EC sensor 401 is operated to monitor only a relative variation in the course of time without determining salts accumulation, and therefore calibration of the EC sensor 401 using the reference culture solution 106 is not necessarily indispensable.

[Overall Configuration of Fertigation System]

The above-described second salts accumulation determination method requires, depending on the climate condition, continuous measurement of the EC value for a long period from a week to a month or so. Although it is inefficient to prepare the EC sensor 102 and the data logger 103 only for determination of salts accumulation, the cost-effectiveness of the entire system is high when they are provided as an optional function of the fertigation system.

Accordingly, a fertigation system under development by the inventors will be described below, and subsequently description will be provided as to how the second salts accumulation determination method is performed in the fertigation system.

Figure 5:
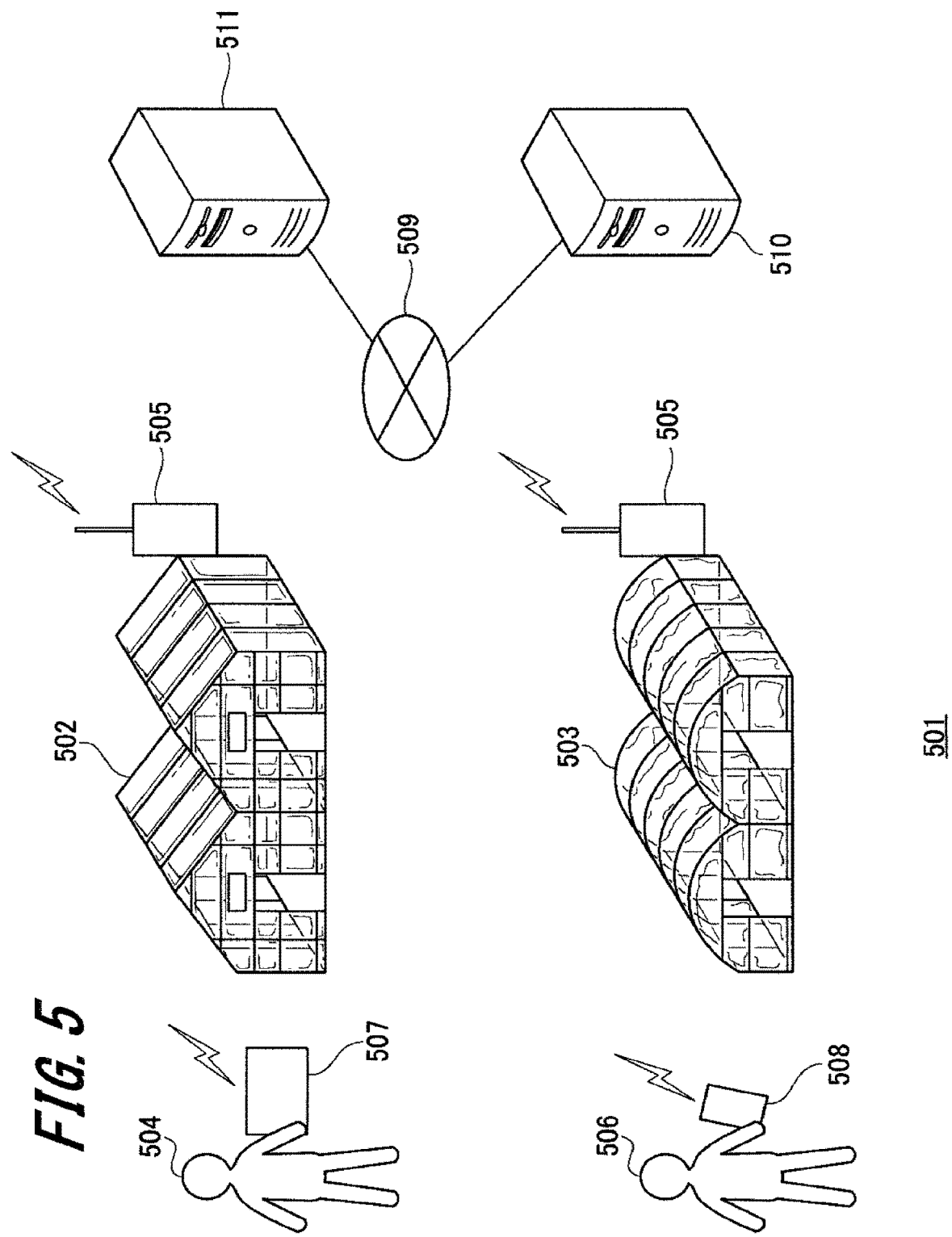
FIG. 5 is a schematic diagram of a fertigation system according to an embodiment of the present invention.

FIG. 5 is a schematic diagram of a fertigation system 501 according to an embodiment of the present invention.

The fertigation system 501 is introduced in a crop cultivation facility for mitigating the influence of weather change, such as a greenhouse 502 or a vinyl house 503, i.e., a greenhouse.

A first agriculture worker 504 has introduced the fertigation system 501 in the greenhouse 502. The greenhouse 502 has a controller 505 installed therein. In addition, a second agriculture worker 506 has introduced the fertigation system 501 in the vinyl house 503. The vinyl house 503 also has the controller 505 installed therein.

As thus described, the controller 505 is designed to be flexibly adaptable to facilities of various farming families.

In addition, the first agriculture worker 504 operates a tablet terminal 507 to provide the fertigation system 501 with instructions when necessary. Similarly, the second agriculture worker 506 operates a smartphone 508 to provide the fertigation system 501 with instructions when necessary.

The controller 505, the tablet terminal 507, and the smartphone 508, being connected to the Internet 509 via wireless communication, perform communication with a fertigation control server 510. Note that, hereafter, each of the tablet terminal 507 and the smartphone 508 will be simply referred to as "terminal" unless otherwise distinguished.

The controller 505 transmits information of various sensors installed in facilities of farming families to the fertigation control server 510, receives control information for supplying culture solution from the fertigation control server 510, and supplies crops with culture solution in an appropriate amount.

The terminal of the tablet terminal 507 or the smartphone 508, upon receiving operation of an agriculture worker, transmits information, such as type of crops being cultivated, start and end of cultivation of crops, fine-adjustment of the amount of fertilization, or the like to the fertigation control server 510.

In addition, the fertigation control server 510 acquires, from a weather forecast server 511 when necessary, weather forecast of the area in which a farming family is located, and uses it to perform fine-adjustment of the amount of fertilization or various additional functions described below.

In other words, from the viewpoint of devices connected to the Internet 509, the fertigation system 501 includes the controller 505, the terminal, and the fertigation control server 510.

The fertigation system 501 is a so-called web-based client-server system. In particular, the fertigation control server 510 includes a group of a plurality of servers, i.e., cloud, in view of usability. In the present embodiment, the fertigation control server 510 is expressed as a single server for simplicity of explanation.

Figure 6:
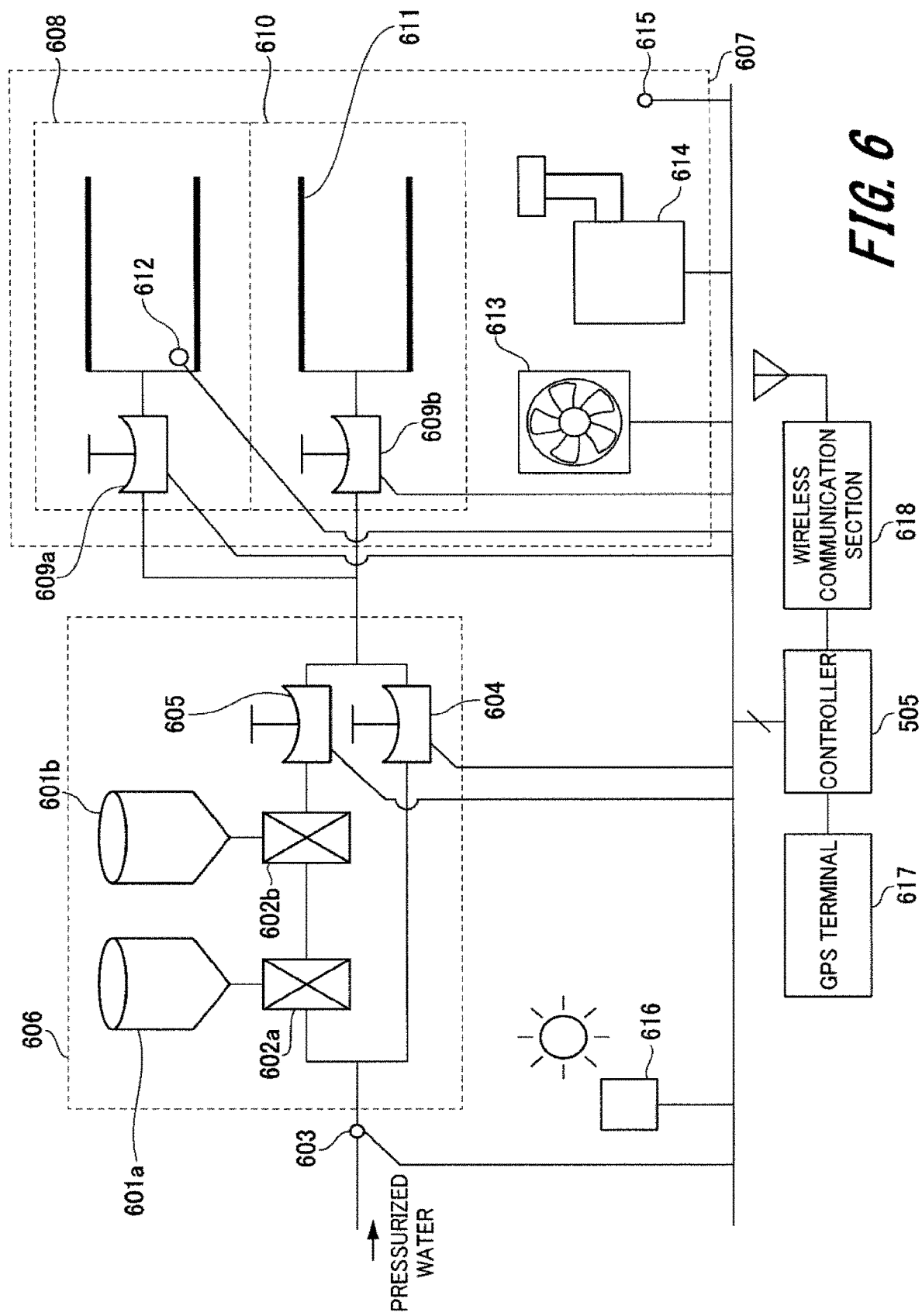
FIG. 6 is a block diagram schematically illustrating facilities in a farming family.

FIG. 6 is a block diagram schematically illustrating facilities in a farming family. FIG. 6 describes devices connected to the controller 505.

The controller 505 installed in a farming family controls a facility which prepares culture solution and supplies it to the greenhouse on the basis of the control information received from the fertigation control server 510 connected to the Internet 509.

A first liquid fertilizer tank 601*a* and a second liquid fertilizer tank 601*b*, which are the basis of culture solution, are installed in the farming family.

The first liquid fertilizer tank 601*a* has a first liquid fertilizer mixer 602*a* connected thereto. The second liquid fertilizer tank 601*b* has a second liquid fertilizer mixer 602*b* connected thereto.

Hereafter, each of the first liquid fertilizer tank 601*a* and the second liquid fertilizer tank 601*b* will be referred to as a liquid fertilizer tank 601 unless otherwise distinguished in particular. Similarly, each of the first liquid fertilizer mixer 602*a* and the second liquid fertilizer mixer 602*b* will be referred to as a liquid fertilizer mixer 602 unless otherwise distinguished in particular.

The liquid fertilizer tank 601 has stored therein high-concentration liquid fertilizer, which is fertilizer dissolved in water. The first liquid fertilizer tank 601*a* and the second liquid fertilizer tank 601*b* have different types of liquid fertilizer stored therein.

The liquid fertilizer mixer 602 is a device which uses water pressure of pressurized water, such as city water, (hereinafter referred to as "pressurized water") to mix liquid fertilizer in the liquid fertilizer tank 601 with water by a predetermined ratio. Note that a flow rate sensor 603 is installed at the water source side where the pressurized water is supplied.

As can be seen in FIG. 6, the first liquid fertilizer mixer 602*a* and the second liquid fertilizer mixer 602*b* are serially connected, so that culture stock solution acquired by mixing liquid fertilizer of the first liquid fertilizer tank 601*a* and liquid fertilizer of the second liquid fertilizer tank 601*b* is discharged from the second liquid fertilizer mixer 602*b*.

Discharge of pressurized water is controlled by a water supply valve 604. Discharge of culture stock solution from the second liquid fertilizer mixer 602*b* is controlled by a culture stock solution supply valve 605.

The controller 505 controls the water supply valve 604 and the culture stock solution supply valve 605 so that only an appropriate amount of culture solution in an appropriate concentration is supplied to the crops.

The discharge sides of the water supply valve 604 and the culture stock solution supply valve 605 are connected to a single pipe, so that culture solution is supplied to one or more discharge valves.

As thus described, the liquid fertilizer tank 601, the liquid fertilizer mixer 602, the water supply valve 604, and the culture stock solution supply valve 605 are included in a culture solution preparing section 606 which prepares culture solution to be supplied to the discharge valves.

There can be formed various variations of the configuration of the culture solution preparing section 606.

For example, installing the first culture stock solution supply valve and the second culture stock solution supply valve in parallel allows for selecting culture stock solution depending on the crops.

In addition, for example, with the water supply valve 604 removed, the first culture stock solution supply valve and the second culture stock solution supply valve which supply a same type of high-concentration liquid fertilizer are installed in parallel so that the second culture stock solution supply valve supplies culture stock solution of a minimum concentration. As thus described, the culture solution preparing section 606 can be formed without the water supply valve 604.

The discharge sides of the water supply valve 604 and the culture stock solution supply valve 605 are connected to a single pipe, so that liquid is supplied to one or more discharge valves.

In FIG. 6, as an example, a first discharge valve 609*a* is installed in a first partition 608 belonging to a greenhouse 607, and a second discharge valve 609*b* is installed in a second partition 610. Hereafter, each of the first discharge valve 609*a* and the second discharge valve 609*b* will be referred to as a discharge valve 609 unless otherwise distinguished. In addition, hereinafter, each of the first partition 608 and the second partition 610 installed in a greenhouse to cultivate crops will be simply abbreviated as a "partition" unless otherwise distinguished.

The fertigation system 501 of the present embodiment is capable of cultivating different types of crops, or crops with shifted planting times, for each partition in the greenhouse 607 having the discharge valves 609 installed therein, by controlling the water supply valve 604 and the culture stock solution supply valve 605, and a plurality of discharge valves 609. In other words, when the second discharge valve 609*b* is closed and the first discharge valve 609*a* is opened, culture solution in an amount and concentration suitable for a first crop being cultivated in the first partition 608 is supplied. When, on the other hand, the first discharge valve 609*a* is closed and the second discharge valve 609*b* is opened, culture solution in an amount and concentration suitable for a second crop, which is different from the first crop, is supplied to the second partition 610. In other words, it is possible to share the controller 505 and a system for preparing culture solution (the liquid fertilizer tank 601, the liquid fertilizer mixer 602, the water supply valve 604, the culture stock solution supply valve 605, and the flow rate sensor 603) for different types of crops or crops with shifted planting times.

In addition, it is not always necessary to shift the type or planting time of crops for each of the discharge valves 609. Since the discharge valve 609 has a maximum tolerable flow rate, overloading an irrigation tube 611 connected thereto may exceed the durability capacity of the discharge valve 609 and may damage the discharge valve 609. Accordingly, the length or the like of the irrigation tube 611 connectable to the discharge valves 609 is determined in accordance with the culture solution supply capacity of the irrigation tube 611 and the maximum tolerable flow rate of the discharge valves 609. When it is desired to lay the irrigation tube 611 with a length exceeding the determined length in the partition, it is necessary to separately install a new unit of the discharge valve 609.

The partition installed in the greenhouse 607 has one or more units of the irrigation tube 611 laid therein.

The irrigation tube 611 has a plurality of holes provided at a regular interval for discharging culture solution. The tip of the irrigation tube 611 is closed with an end cap which is not illustrated.

The longer the irrigation tube 611, the larger the number of holes becomes, whereby the culture solution supply amount per unit time increases. In other words, the culture solution supply amount by the irrigation tube 611 turns out to be a figure calculated by multiplying the culture solution supply capacity per unit length by the length of the irrigation tube 611 to be laid.

Generally, it is supposed that a plurality of units of the irrigation tube 611 of a same type is to be connected in parallel to the discharge valves 609. This is because serial connection causes time difference in supply of culture solution between the tip and the root of the irrigation tube 611, and thus requires consideration so as to reduce the time difference as much as possible. In addition, this is because connecting different types of the irrigation tube 611 to the discharge valves 609 results in a difference in the culture solution supply capacity for a partition per unit area, making it impossible to manage the culture solution supply amount.

The partition installed in the greenhouse 607 has one or more units of the irrigation tube 611 laid therein.

The irrigation tube 611 is supplied with culture solution via the discharge valve 609. The culture solution is sprayed from the plurality of holes 801 provided in the irrigation tube 611 onto the ground in the greenhouse 607 having the irrigation tube 611 laid therein.

A soil sensor 612 is inserted into the vicinity of the irrigation tube 611. Note that, although the soil sensor 612 may be installed for each of the discharge valves 609, a plurality of partitions shares the soil sensor 612 in FIG. 6.

The soil sensor 612 outputs the soil water amount, soil EC, and ground temperature as analog voltage signals.

A large-sized greenhouse may be provided with air conditioning equipment. In FIG. 6, the greenhouse 607 has a ventilation fan 613 and a boiler 614 installed therein. In addition, there is also installed an air temperature sensor 615 in order to measure the air temperature in the greenhouse 607.

There is a solar radiation sensor 616 installed in the vicinity of the greenhouse 607. The solar radiation sensor 616 outputs the strength of solar radiation as analog voltage signals.

Analog voltage signals output from the solar radiation sensor 616, the flow rate sensor 603, the soil sensor 612, and the air temperature sensor 615 are input to the controller 505. In addition, the controller 505 controls open/close of each of the water supply valve 604, the culture stock solution supply valve 605, the first discharge valve 609a and the second discharge valve 609b.

As will be described in detail in FIG. 7, the controller 505 includes a publicly known microcomputer. The controller 505 further receives an input of positioning information from a GPS terminal 617 having a function as a positioning information output section. The controller 505 then connects to the Internet 509 via a wireless communication section 618, and transmits and receives information to and from the fertigation control server 510.

The controller 505 transmits measurement data acquired from the solar radiation sensor 616 and the soil sensor 612 to the fertigation control server 510 at a 10-minute interval from sunrise to sunset. The controller 505 then controls the water supply valve 604, the culture stock solution supply valve 605, the first discharge valve 609a, and the second discharge valve 609b, on the basis of the data received from the fertigation control server 510 upon transmitting the measurement data to the fertigation control server 510 everyone or two hours, with regard to each of the first discharge valve 609a and the second discharge valve 609b. Subsequently, the controller 505 transmits the flow-rate data of the culture solution acquired at the above occasion from the flow rate sensor 603 to the fertigation control server 510.

Hereafter, in the present embodiment, the fertigation control server 510 is supposed to transmit control data to the controller 505 every one hour.

The controller 505 controls one of the culture solution preparing sections 606. The culture solution preparing section 606 supplies culture solution to only one of the discharge valves 609. In other words, the plurality of discharge valves 609 connected in parallel to the culture solution preparing section 606 is exclusively controlled in a time-division manner. Therefore, as the number of discharge valves 609 controlled by the controller 505 increases, a time for controlling the opening of the discharge valves 609 by the controller 505 becomes longer for the sake of controlling the discharge valves 609 in a time-division manner, and await time during which the controller 505 waits for an instruction from the fertigation control server 510 becomes shorter. In a case where there is no wait time, the configuration of the facilities mainly based on the discharge valves 609 is not appropriate and therefore it becomes necessary to separately install a new unit of the culture solution preparing section 606.

In addition, an agriculture worker can use a terminal to arbitrarily change the amount of the standard soil water and the reference soil EC described below.

[Hardware Configuration of Controller 505]

Figure 7:
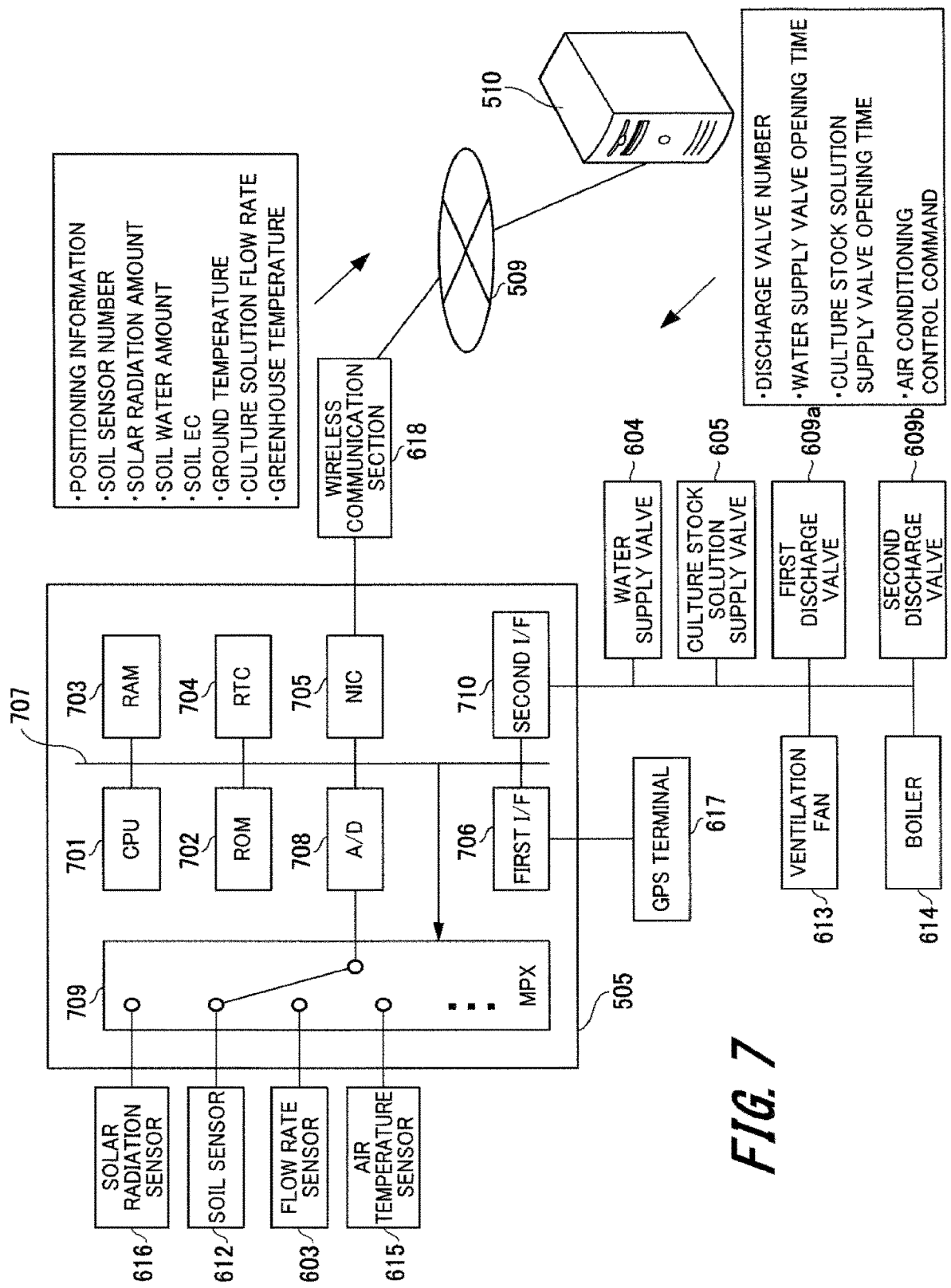
FIG. 7 is a block diagram illustrating a hardware configuration of a controller.

FIG. 7 is a block diagram illustrating a hardware configuration of the controller 505. Here, the fertigation control server 510 connected to the Internet 509 is also illustrated in order to describe the outline of information transmitted and received to and from the fertigation control server 510.

The controller 505 including a microcomputer has a CPU 701, a ROM 702, a RAM 703, a real time clock (hereinafter abbreviated as "RTC, and also abbreviated in FIG. 7 as "RTC") 704 for outputting date-and-time information, an NIC (Network Information Card) 705, and a first serial interface 706 (abbreviated as "first I/F" in FIG. 7), which are connected to a bus 707.

Furthermore, an A/D converter 708 (abbreviated as "A/D" in FIG. 7) connected to the bus 707 has a multiplexer 709 (abbreviated as "MPX" in FIG. 7) connected thereto. The multiplexer 709 has the solar radiation sensor 616, the flow rate sensor 603, the soil sensor 612, and the air temperature sensor 615 connected thereto.

Furthermore, a second serial interface 710 (abbreviated as "second I/F" in FIG. 7) connected to the bus 707 has the water supply valve 604, the culture stock solution supply valve 605, the first discharge valve 609a, the second discharge valve 609b, the ventilation fan 613, and the boiler 614 connected thereto.

The controller 505 receives positioning information output from the GPS terminal 617 via the first serial interface 706.

The controller 505 is connected to the Internet 509 via the wireless communication section 618 connected to the NIC 705. The controller 505 then transmits, to the fertigation control server 510, positioning information output from the GPS terminal 617, a soil sensor number for distinguishing the soil sensor 612, the solar radiation amount output from the solar radiation sensor 616, soil water amount, soil EC, and ground temperature output from the soil sensor 612, the flow rate of the culture solution output from the flow rate sensor 603, and the greenhouse temperature output from the air temperature sensor 615. Furthermore, the controller 505 receives, from the fertigation control server 510, a discharge valve number for distinguishing the first discharge valve 609a and the second discharge valve 609b, a water supply valve opening time, a culture stock solution supply valve opening time, and an air conditioning control command.

[Software Function of Controller 505]

Figure 8:
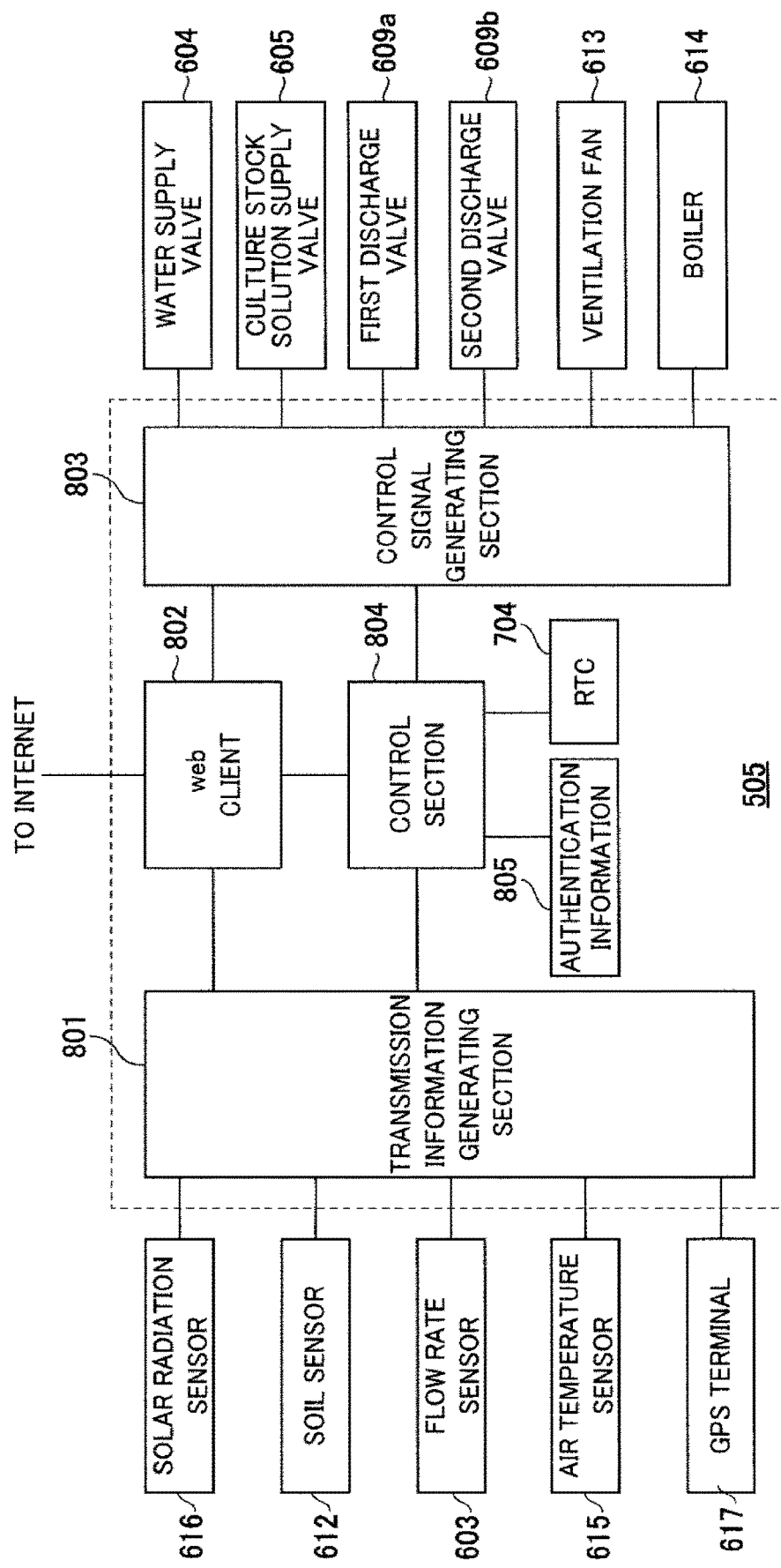
FIG. 8 is a block diagram illustrating a software function of a controller.

FIG. 8 is a block diagram illustrating a software function of the controller 505.

Information output from the solar radiation sensor 616, the soil sensor 612, the flow rate sensor 603, the air temperature sensor 615, and the GPS terminal 617 is converted into text stream data based on the publicly known XML (Extensible Markup Language) specification, for example, by a transmission information generating section 801. The XML text stream data is then transmitted to the fertigation control server 510 using a protocol, such as HTTPS (Hyper Text Transfer Protocol Secure), by a web client 802.

The web client 802 passes the text stream data received from the fertigation control server 510 to a control signal generating section 803.

The control signal generating section 803 takes out, from the text stream data, a discharge valve number for distinguishing the first discharge valve 609*a* and the second discharge valve 609*b*, the water supply valve opening time, and the culture stock solution supply valve opening time, and controls the water supply valve 604, the culture stock solution supply valve 605, the first discharge valve 609*a*, the second discharge valve 609*b*, the ventilation fan 613, and the boiler 614.

A control section 804 has a function as a scheduler.

The control section 804 receives date-and-time information from an RTC 704 and, upon recognizing that a predetermined time has been reached, transmits authentication information 805 to the fertigation control server 510 via the web client 802 for authentication. Upon normally performing authentication, the control section 804 activates the transmission information generating section 801. When control information is included in the text stream data received by the web client 802 from the fertigation control server 510, the control section 804 activates the control signal generating section 803.

The authentication information 805 is a device ID and password of the controller 505 stored in the ROM 702. The device ID is information for uniquely identifying the controller 505.

As can be seen in FIG. 8, the controller 505 has no function of performing a calculation for controlling the water supply valve 604, the culture stock solution supply valve 605, the first discharge valve 609*a*, and the second discharge valve 609*b*, on the basis of data acquired from the solar radiation sensor 616 and the soil sensor 612. Accordingly, the data for controlling the water supply valve 604, the culture stock solution supply valve 605, the first discharge valve 609*a*, the second discharge valve 609*b*, the ventilation fan 613, and the boiler 614 is generated by the fertigation control server 510.

In other words, the controller 505 can be realized by a microcomputer which is inexpensive and has a relatively low calculation ability. The complicated and high-level calculation process for generating data for controlling the water supply valve 604, the culture stock solution supply valve 605, the first discharge valve 609*a*, and the second discharge valve 609*b* is performed by the fertigation control server 510. Simplifying the hardware configuration of the client makes it possible for a personal enterprise to introduce the fertigation system 501 of the present embodiment relatively easily.

[Hardware Configuration of Fertigation Control Server 510]

Figure 9:
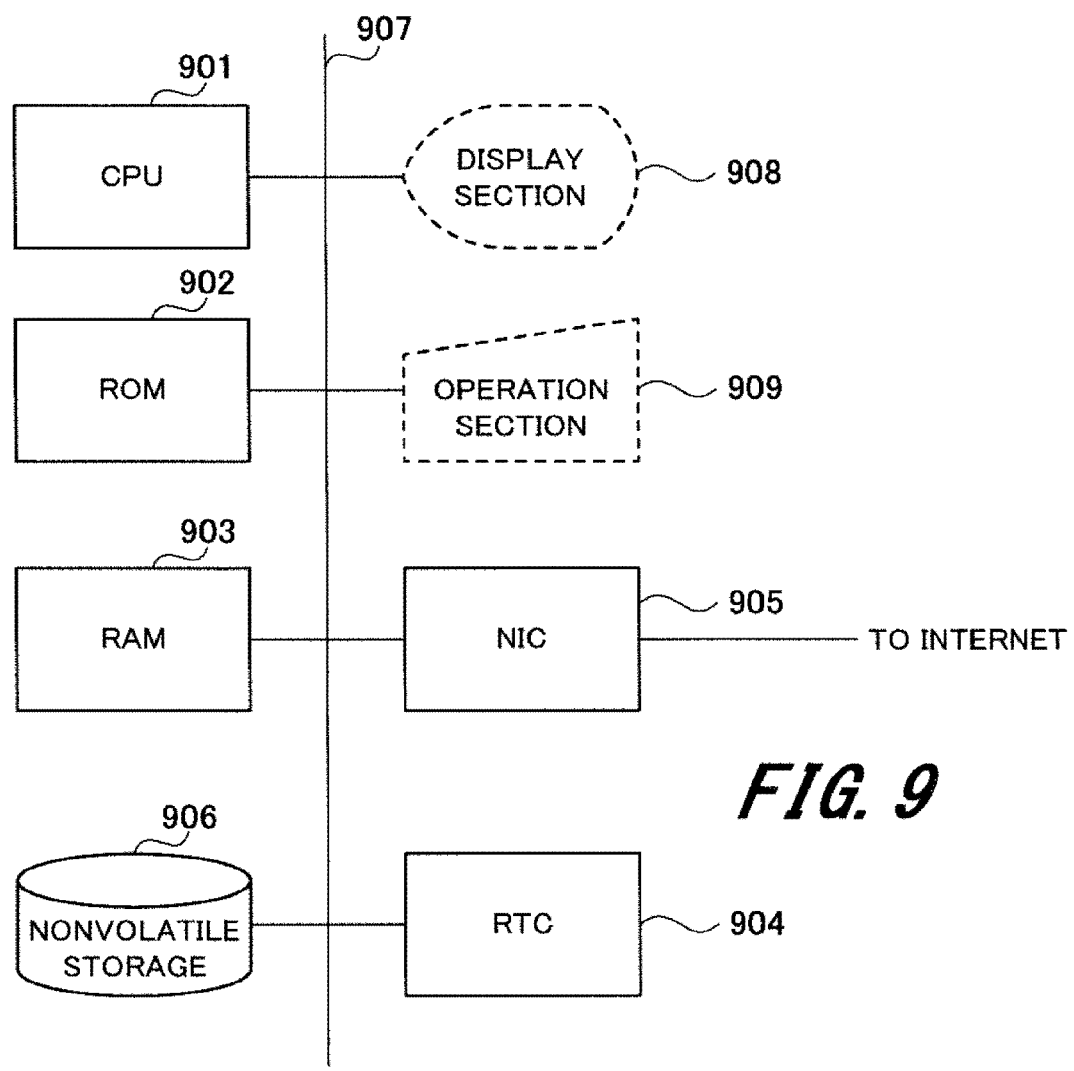
FIG. 9 is a block diagram illustrating a hardware configuration of a fertigation control server.

FIG. 9 is a block diagram illustrating a hardware configuration of the fertigation control server 510.

The fertigation control server 510 including a publicly known computer has connected, to a bus 907, a CPU 901, a ROM 902, a RAM 903, an RTC 904, an NIC 905 connected to the Internet 509, and a nonvolatile storage 906. The nonvolatile storage 906 has stored therein a publicly known network OS, a program for causing a computer to function as the fertigation control server 510, and various databases described below.

Note that a general PC can also be used as the fertigation control server 510. In such a case, a display section 908 and an operation section 909 are connected to the bus 907. However, the display section 908 and the operation section 909 are not necessarily required for the fertigation control server 510.

[Software Function of Fertigation Control Server 510]

Figure 10:
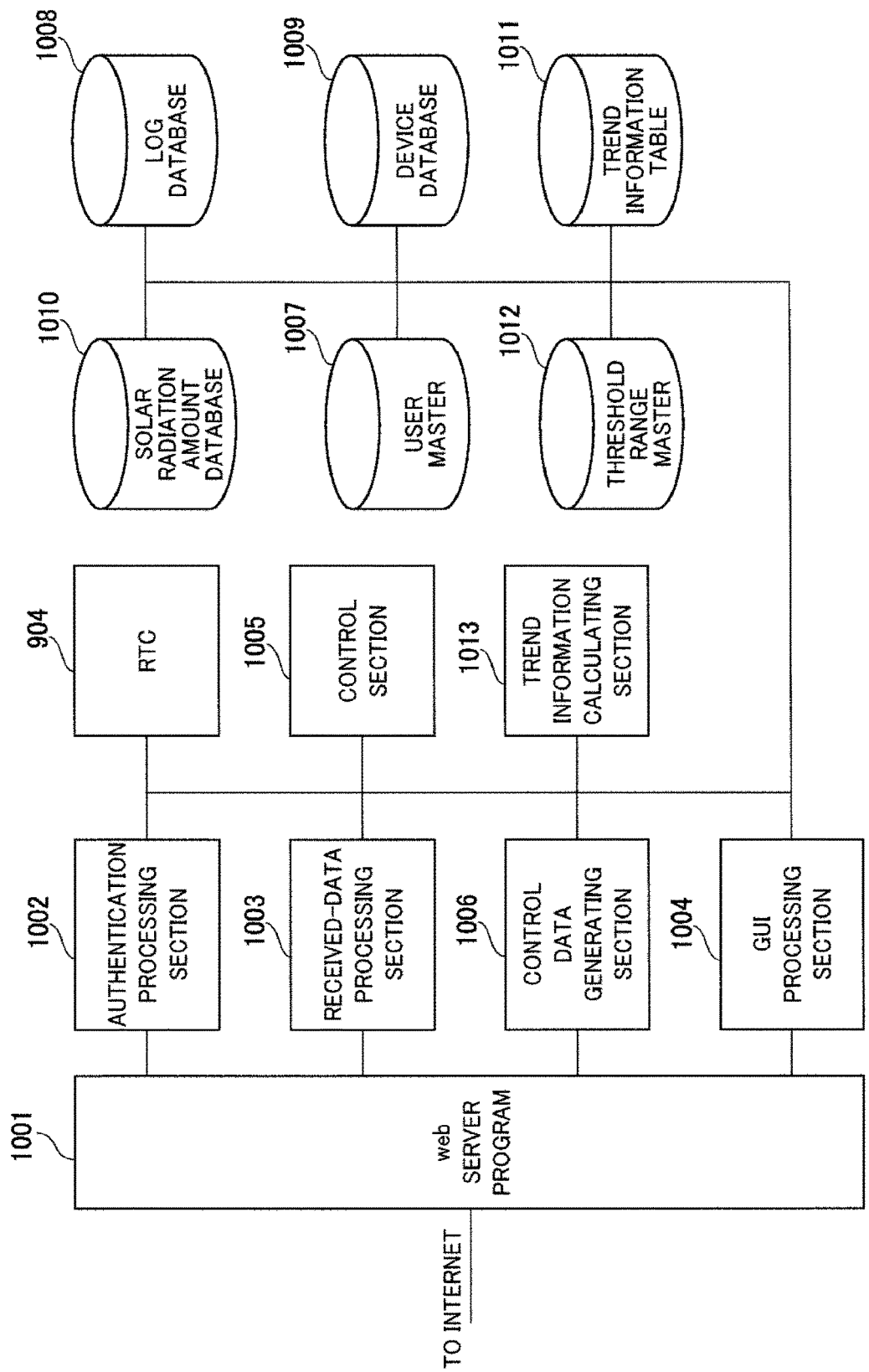
FIG. 10 is a block diagram illustrating a software function of a fertigation control server.

FIG. 10 is a block diagram illustrating a software function of the fertigation control server 510.

The fertigation control server 510 is an HTTPS web server.

A web server program 1001 communicates via HTTPS with the controller 505 which is a client and, depending on the content of communication, activates an authentication processing section 1002, a received-data processing section 1003, and a GUI processing section 1004. In addition, the web server program 1001 transmits, to the controller 505, information output from a control data generating section 1006 activated by the control section 1005. Note that, although HTTPS usually uses a TCP port number 443, the port number is freely variable in consideration of security.

The authentication processing section 1002, the received-data processing section 1003, the control data generating section 1006, and the GUI processing section 1004 are programs referred to as, for example, CGI (Common Gateway Interface) or applet.

The authentication processing section 1002 authenticates the controller 505 or a terminal, which are clients, referring to a user master 1007 when necessary.

The received-data processing section 1003 records data received from the controller 505 in a log database 1008.

The control data generating section 1006 is activated by the control section 1005, reads data from the log database 1008, a device database 1009, a solar radiation amount database 1010, and a trend information table 1011, generates data to be transmitted to the controller 505, which is a client, and transmits it to the controller 505 via the web server program 1001.

The GUI processing section 1004 forms, on a terminal which is a client, a GUI operation screen for operating the reference soil water amount and the reference soil EC described below, and, in accordance with instructions from the terminal operator, changes the reference soil water amount and the reference soil EC. On this occasion, reference is made to a threshold range master 1012.

The RTC 904 provides a function equivalent to that of the RTC 704 of the controller 505.

The control section 1005 determines whether or not it is necessary to transmit control data for controlling the water supply valve 604, the culture stock solution supply valve 605, and the discharge valves 609 to the controller 505 currently accessing the fertigation control server 510, on the basis of the current time or the like acquired from the RTC 904. Then, the control section 1005, upon determining that it is necessary to transmit control data to the controller 505, activates the control data generating section 1006.

In addition, the control section 1005, which is also provided with a function as a scheduler similarly to the client, activates a trend information calculating section 1013 at midnight. The trend information calculating section 1013 reads the soil water amount and the soil EC from a first log table 1201 of the log database 1008 described below, calculates trend information of the soil water amount and the soil EC for each of the soil sensors 612, and stores the information in the trend information table 1011.

Figure 11:
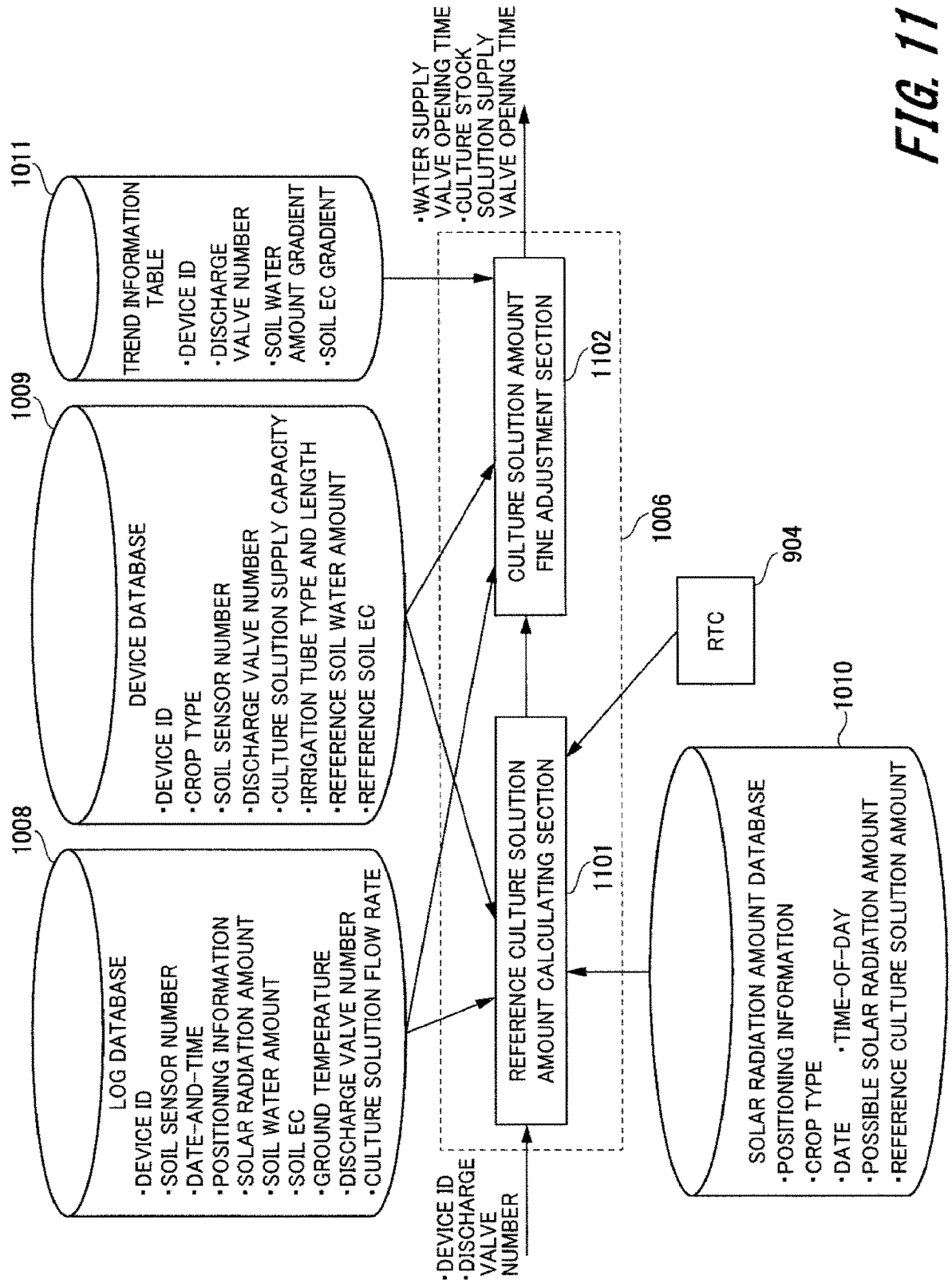
FIG. 11 is a block diagram illustrating a function of a control data generating section.

FIG. 11 is a block diagram illustrating a function of the control data generating section 1006.

The control data generating section 1006 performs the calculation process in two stages.

The control data generating section 1006 first, upon receiving a device ID of the controller 505 currently accessing the fertigation control server 510 from the control section 1005, activates a "reference culture solution amount" calculating section 1101.

The "reference culture solution amount" calculating section 1101 retrieves positioning information, solar radiation amount, and crop type from the log database 1008 by specifying the device ID and the discharge valve number. Subsequently, the "reference culture solution amount" calculating section 1101 calculates a reference culture solution amount, referring to the solar radiation amount database 1010.

Next, a "culture solution amount fine adjustment" section 1102 retrieves the soil water amount and the soil EC of the soil sensor 612 associated with the discharge valve 609 from the log database 1008 by specifying the device ID and the discharge valve number. Subsequently, the "culture solution amount fine adjustment" section 1102 retrieves the reference soil water amount and the reference soil EC from the device database 1009 by specifying the device ID and the discharge valve number. Furthermore, the "culture solution amount fine adjustment" section 1102 retrieves a soil water amount gradient and a soil EC gradient from the trend information table 1011 by specifying the device ID and the discharge valve number. Subsequently, the "culture solution amount fine adjustment" section 1102 performs calculation on the basis of the above-described data to acquire a water supply valve opening time and a culture stock solution supply valve opening time.

[Configuration of Databases]

Figure 12:
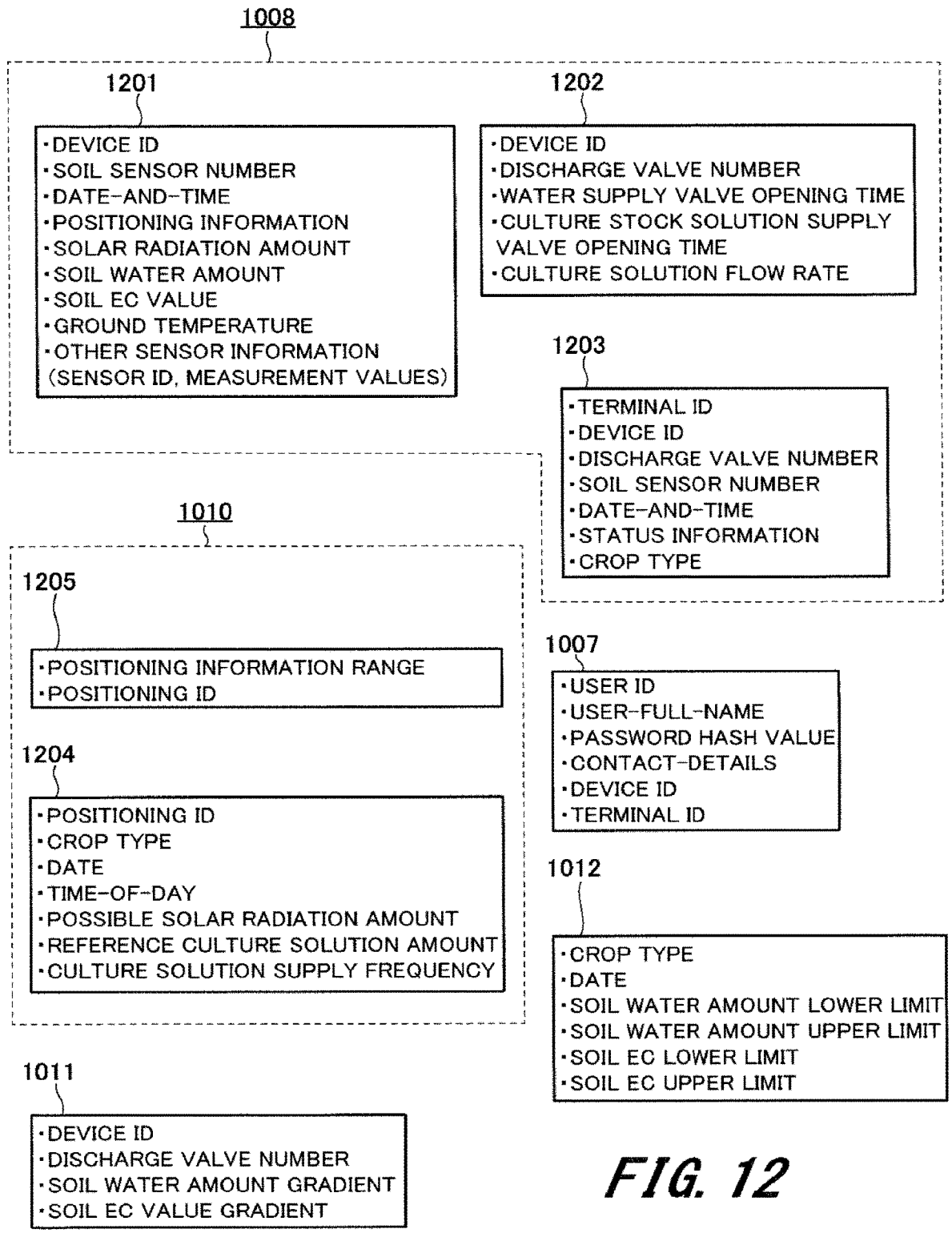
FIG. 12 illustrates configurations of a log database, a solar radiation amount database, a trend information table, a threshold range master, and a user master.

FIG. 12 illustrates a configuration of the log database 1008, the solar radiation amount database 1010, the trend information table 1011, the threshold range master 1012, and the user master 1007.

Figure 13:
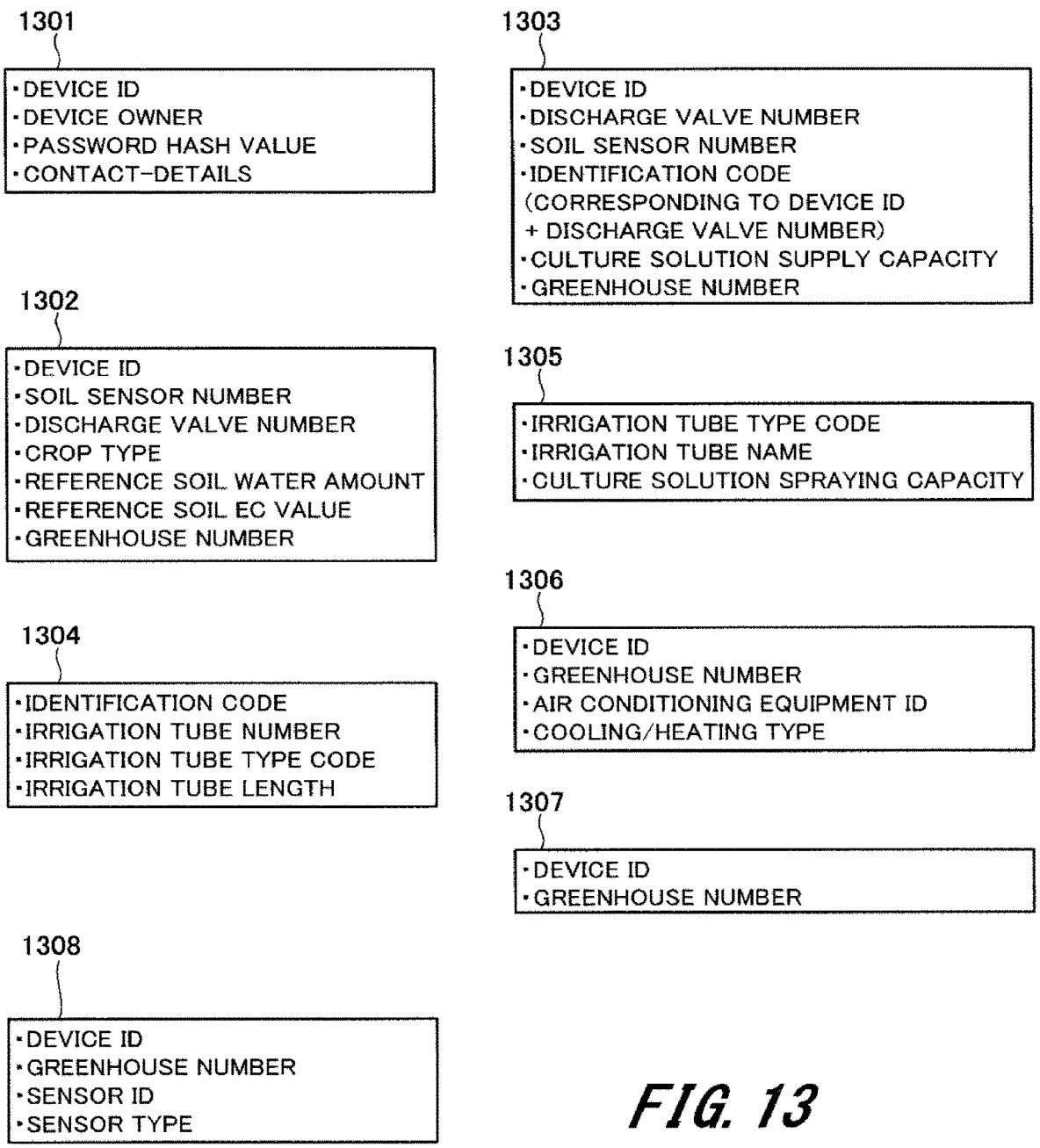
FIG. 13 illustrates a configuration of a device database.

FIG. 13 illustrates a configuration of the device database 1009.

The log database 1008 has the first log table 1201, a second log table 1202, and a third log table 1203.

The solar radiation amount database 1010 has a "solar radiation amount and culture solution amount" table 1204 and a positioning information table 1205.

The devices database 1009 has a devices master 1301, a soil sensor table 1302, a discharge valve table 1303, an irrigation tube table 1304, an irrigation tube master 1305, an air conditioning equipment table 1306, a greenhouse table 1307, and an environment sensor table 1308.

First, configurations of the log database 1008, the solar radiation amount database 1010, the trend information table 1011, the threshold range master 1012, and the user master 1007 will be described, referring to FIG. 12.

The first log table 1201, which may also be referred to as a sensor information table, is a table that stores information received from the controller 505, and has a device ID field, a soil sensor number field, a date-and-time field, a positioning information field, a solar radiation amount field, a soil water amount field, a soil EC field, a ground temperature field, and other sensor information fields.

The device ID field stores a device ID.

The soil sensor number field stores a soil sensor number for uniquely identifying the soil sensor 612 connected to the controller 505 bearing a certain device ID. The controller 505 of the present embodiment can have as many as six units of the soil sensor 612 connected thereto.

The date-and-time field stores a date-and-time when data is received from the controller 505.

The positioning information field stores positioning information of the GPS terminal 617, received from the controller 505.

The solar radiation amount field stores data of the solar radiation amount of the solar radiation sensor 616, received from the controller 505.

The soil water amount field stores data of the soil water amount of the soil sensor 612, received from the controller 505.

The soil EC field stores data of the soil EC of the soil sensor 612, received from the controller 505.

The ground temperature field stores data of ground temperature of the soil sensor 612, received from the controller 505.

The other sensor information fields store sensor IDs of other sensors, such as the air temperature sensor 615 of a greenhouse, and information of measurement values, received from the controller 505.

Note that, in the fertigation system 501 of the present embodiment, ground temperature is not used for calculating the culture solution amount. However, logging the variation of the ground temperature in the first log table 1201, similarly to other information of sensors, allows for verifying correlation or the like with the growth situation of the crops. Since the fertigation control server 510 stores information of a plurality of farming families in the first log table 1201 and the second log table 1202, accumulation of operation results of the server can be used as the so-called "big data" for various analysis.

The second log table 1202 is a table that stores information transmitted to the controller 505 and information acquired as a result of performing control by the controller 505 for supplying culture solution, and has a device ID field, a discharge valve number field, a "water supply valve opening time" field, a "culture stock solution supply valve opening time" field, and a "culture solution flow rate" field.

The device ID field is identical to the field bearing the same name in the first log table 1201.

The discharge valve number field stores a discharge valve number for uniquely identifying the discharge valve 609 connected to the controller 505 bearing a certain device ID.

The "water supply valve opening time" field stores a period during which the water supply valve is opened.

The "culture stock solution supply valve opening time" field stores a period during which the culture stock solution supply valve is opened.

The "culture solution flow rate" field stores data of the culture solution flow rate of the flow rate sensor 603 received from the controller 505. In other words, the information of the flow rate sensor 603 is information acquired as a result of performing control of culture solution supply.

The third log table 1203, which may also be referred to as a status information table, is a table that stores information received from a terminal, and has a terminal ID field, a device ID field, a discharge valve number field, a soil sensor number field, a date-and-time field, a status information field, and a crop type field.

The terminal ID field stores a terminal ID of the terminal operated by an agriculture worker.

The device ID field is identical to the field bearing the same name in the first log table 1201.

The discharge valve number field is identical to the field bearing the same name in the second log table 1202.

The soil sensor number field is identical to the field bearing the same name in the first log table 1201.

The date-and-time field is identical to the field bearing the same name in the first log table 1201.

The status information field stores status information received from a terminal.

The crop type field stores a type of crop received from a terminal.

The third log table 1203 stores information indicating a state of a partition in which a crop is cultivated, the partition being associated with a unit of the discharge valve 609 identified by a device ID and a discharge valve number. Specifically, whether or not a crop is being cultivated in the partition, or what is a type of the crop. Furthermore, the status information stored in the third log table 1203 is also required for a salts accumulation determination function described below.

The positioning information table 1205 includes a positioning information range field and a positioning ID field.

The positioning information range field stores information indicating a range over a map supposed to be the basis of calculating equal culture solution amounts.

The positioning ID field stores a positioning ID for uniquely identifying a positioning information range field.

The "solar radiation amount and culture solution amount" table 1204 has a positioning ID field, a crop type field, a date field, a time-of-day field, a "possible solar radiation amount" field, and a "reference culture solution amount" field.

The positioning ID field is identical to the field bearing the same name in the positioning information table 1205.

The crop type field is identical to the field bearing the same name in the third log table 1203.

The date field stores a date when a solar radiation amount is measured.

The time-of-day field stores a time of day when a solar radiation amount is measured.

The "possible solar radiation amount" field stores a possible solar radiation amount at a date-and-time identified in the date field and the time-of-day field. The possible solar radiation amount is a possible calculation-based maximum solar radiation amount (solar radiation amount during a fine weather) at a latitude and longitude of a certain place on a certain date-and-time, which is also referred to as "potential solar radiation amount".

The "reference culture solution amount" field stores a culture solution amount with a possible solar radiation amount on a date-and-time identified in the date field and the time-of-day field.

The "solar radiation amount and culture solution amount" table 1204 has registered therein a possible solar radiation amount acquired from the Japan Meteorological Agency, corresponding to the latitude and longitude for 365 days a year. Also a culture solution amount required for a certain type of crop corresponding to the possible solar radiation amount in the land on the specific day is recorded in the "reference culture solution amount" field.

First, the positioning information acquired from the GPS terminal 617 connected to the controller 505 is matched with the positioning information table 1205 to identify a positioning ID. In other words, the nearest observation spot of the solar radiation amount is identified.

Next, a record of the "solar radiation amount and culture solution amount" table 1204 is identified in accordance with the identified positioning ID, the crop type acquired from the third log table 1203, and the date-and-time information acquired from the RTC 904.

Subsequently, the information of the solar radiation amount recorded in the first log table 1201 is compared with the possible solar radiation amount recorded in the identified record of the "solar radiation amount and culture solution amount" table 1204 to calculate a ratio of the solar radiation amount, and the ratio is multiplied by a reference culture solution amount. In other words, the ratio of the current solar radiation amount against the possible solar radiation amount is calculated, and the reference culture solution amount is adjusted in accordance with the ratio. For example, in a case of a solar radiation amount as much as 50% of the possible solar radiation amount, the reference culture solution amount is multiplied by 50%.

The user master 1007 has a user ID field, a user-full-name field, a password hash value field, a contact-information field, and a device ID field.

The user ID field stores a user ID, which is identification information for uniquely identifying an agriculture worker.

The user-full-name field stores a full name of an agriculture worker.

The password hash value field stores a hash value of a password for authenticating an agriculture worker identified by a user ID stored in the user ID field.

The contact-information field stores information indicating contact information of an agriculture worker.

The device ID field stores a device ID of the controller 505 used by an agriculture worker.

The trend information table 1011 has a device ID field, a discharge valve number field, a "soil water amount gradient" field, and a "soil EC value gradient" field.

The device ID field is identical to the field bearing the same name in the first log table 1201.

The discharge valve number field is identical to the field bearing the same name in the second log table 1202.

The "soil water amount gradient" field stores a soil water amount gradient measured by a soil sensor associated with the discharge valve 609 bearing a discharge valve number recorded in the first log table.

The "soil EC value gradient" field stores a soil EC value gradient measured by a soil sensor associated with the discharge valve 609 bearing a discharge valve number recorded in the first log table.

The soil water amount gradient and the soil EC value gradient are information necessary for a fine-adjustment process of the culture solution amount in the above-described "culture solution amount fine adjustment" section.

The threshold range master 1012 has a crop type field, a date field, a "soil water amount lower limit" field, a "soil water amount upper limit" field, a "soil EC lower limit" field, and a "soil EC upper limit" field.

The crop type field is identical to the field bearing the same name in the third log table 1203.

The date field is identical to the field bearing the same name in the "solar radiation amount and culture solution amount" table.

The "soil water amount lower limit" field stores a lower limit of a target soil water amount.

The "soil water amount upper limit" field stores an upper limit of a target soil water amount.

The "soil EC lower limit" field stores a lower limit of a target soil EC value.

The "soil EC upper limit" field stores an upper limit of a target soil EC value.

Next, a configuration of the device database 1009 will be described, referring to FIG. 13.

A devices master 1301 is a table of the controller 505 and has a device ID field, a device owner field, a password hash value field, and a contact-information field.

The device ID field is identical to the field bearing the same name in the first log table 1201.

The device owner field stores a full name or a corporate name of an owner of the controller 505.

The password hash value field has stored therein a hash value of a password for authenticating the device ID of the controller 505.

The contact-information field stores information indicating contact information of the owner of the controller 505.

The soil sensor table 1302 is a table of the soil sensor 612, and has a device ID field, a soil sensor number field, a discharge valve number field, a crop type field, a "reference soil water amount" field, a reference soil EC field, and a greenhouse number field.

The device ID field is identical to the field bearing the same name in the first log table 1201.

The soil sensor number field is identical to the field bearing the same name in the first log table 1201.

The discharge valve number field stores one or more discharge valve numbers of the discharge valves 609 belonging to the soil sensor 612 stored in the soil sensor number field.

The crop type field stores information indicating the type of crop being cultivated using the discharge valve 609 designated in the discharge valve number field.

The "reference soil water amount" field stores a reference soil water amount for a crop being cultivated using the discharge valve 609 designated in the discharge valve number field.

The reference soil EC field stores a reference EC for a crop being cultivated using the discharge valve 609 designated in the discharge valve number field.

The greenhouse number field stores a greenhouse number of the greenhouse in which the soil sensor 612 is laid.

The crops being cultivated in a greenhouse are managed by at least one unit of the soil sensor 612. Accordingly, the soil sensor table 1302 has a crop type field provided therein. The crop type to be written in the crop type field is copied from crop type field of the third log table.

The discharge valve table 1303 is a table of the discharge valve 609, and has a device ID field, a discharge valve number field, a soil sensor number field, an identification code field, a "culture solution supply capacity" field, and a greenhouse number field.

The device ID field is identical to the field bearing the same name in the first log table 1201.

The discharge valve number field is identical to the field bearing the same name in the second log table 1202.

The soil sensor number field stores one or more soil sensor numbers of the soil sensors 612 belonging to the discharge valve 609 stored in the discharge valve number field.

The identification code field stores an identification code for uniquely identifying the discharge valve 609 bearing a certain discharge valve number of a certain device ID. The identification code may be a combination of a device ID and a discharge valve number. The identification code is used in the irrigation tube table 1304 described below.

The "culture solution supply capacity" field stores a culture solution supply amount per unit time of the discharge valve 609 stored in the discharge valve number field. The value is stored in the field by supplying water to the discharge valve 609 and measuring the liquid supply amount per unit time of the discharge valve 609, for the purpose of measuring the state of facilities when introducing the fertigation system of the present embodiment in a farming family.

The greenhouse number field is identical to the field bearing the same name in the soil sensor table 1302.

The irrigation tube table 1304 is a table of the irrigation tube 611 and has an identification code field, an irrigation tube number field, an "irrigation tube type code" field, and an irrigation tube length field.

The identification code field is identical to the field bearing the same name in the discharge valve table 1303.

The irrigation tube number field stores one or more numbers for uniquely identifying the irrigation tubes 611 connected to the discharge valve 609 identified by an identification code.

The "irrigation tube type code" field stores information indicating the type of the irrigation tube 611 identified in the irrigation tube number field.

The irrigation tube length field stores information indicating the length of the irrigation tube 611 identified in the irrigation tube number field.

The irrigation tube master 1305 has an "irrigation tube type code" field, an irrigation tube name field, and a "culture solution spraying capacity" field.

The "irrigation tube type code" field is identical to the field bearing the same name in the irrigation tube table 1304.

The irrigation tube name field stores a manufacturing company name and a product name of the irrigation tube 611.

The "culture solution spraying capacity" field stores culture solution spraying amount per unit length and unit time of the irrigation tube 611 identified by the type code of the irrigation tube 611.

[Relation Among Farming Family Facilities]

Here, the relation among the first log table 1201, the second log table 1202, the soil sensor table 1302, the discharge valve table 1303, the irrigation tube table 1304, the air conditioning equipment table 1306, the greenhouse table 1307, and the environment sensor table 1308 will be described once.

Figure 14:
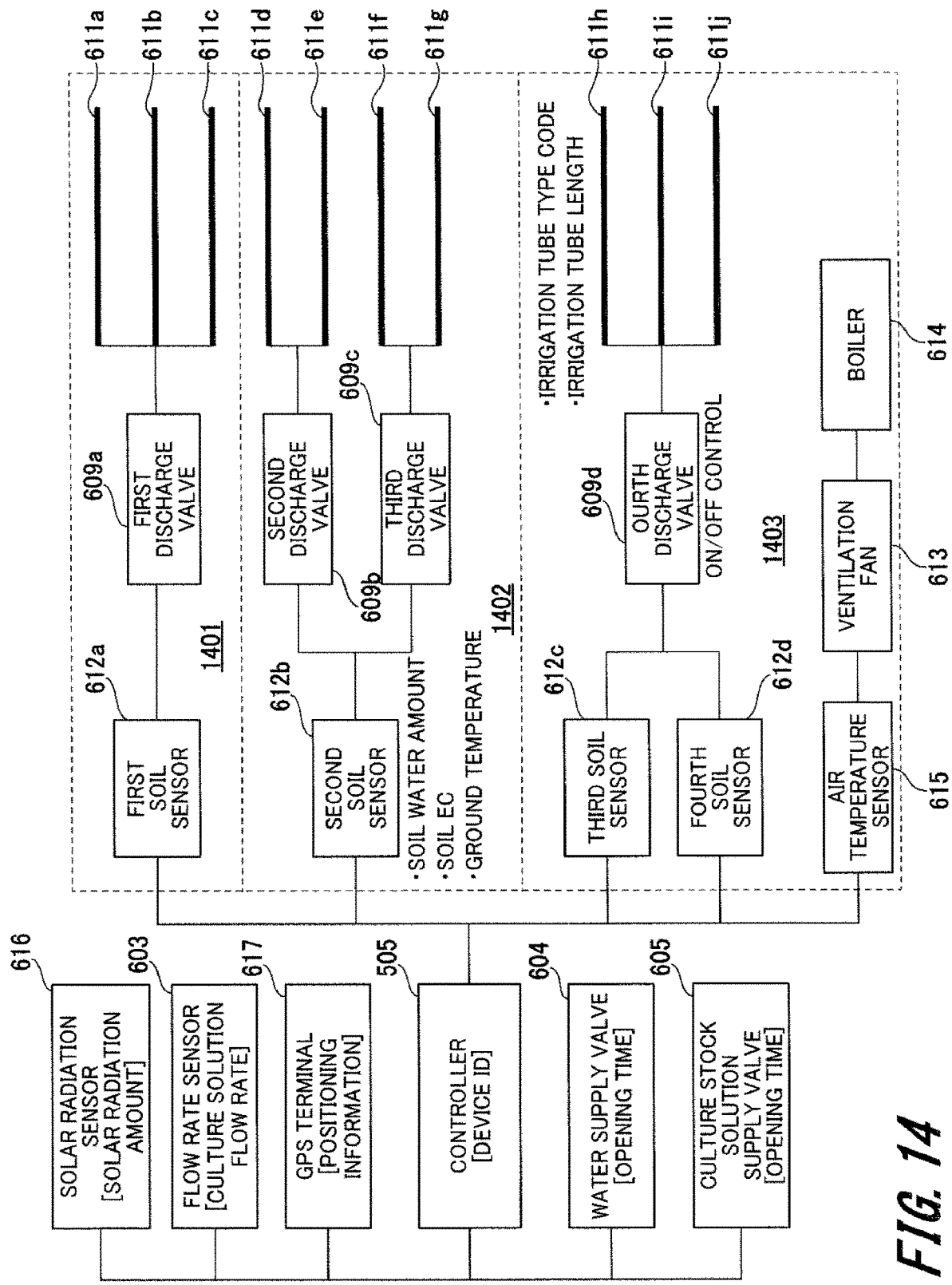
FIG. 14 is a schematic diagram illustrating relations between a controller and various sensors and devices connected thereto.

FIG. 14 is a schematic diagram illustrating relations between a controller 505 and various sensors and devices connected thereto.

A single unit of the controller 505 is associated with a single unit of the solar radiation sensor 616, a single unit of the flow rate sensor 603, a single unit of the GPS terminal 617, a single unit of the water supply valve 604, and a single unit of the culture stock solution supply valve 605. They are all in a one-to-one relation. In other words, the solar radiation amount, the culture solution flow rate, the positioning information, the water supply valve opening time, and the culture stock solution supply valve opening time, with regard to a device ID, are associated with each other in a one-to-one manner.

In FIG. 14, there are provided three greenhouses, namely, a first greenhouse 1401, a second greenhouse 1402, and a third greenhouse 1403.

The first greenhouse 1401 has laid therein a first soil sensor 612*a* and the first discharge valve 609*a*.

The first discharge valve 609*a* has laid therein a first irrigation tube 611*a*, a second irrigation tube 611*b*, and a third irrigation tube 611*c*.

Therefore, when the first discharge valve 609*a* is opened with other discharge valves 609 being closed, the culture solution being supplied from the water supply valve 604 and the culture stock solution supply valve 605 are sprayed on the soil in the first greenhouse 1401 by the first irrigation tube 611*a*, the second irrigation tube 611*b*, and the third irrigation tube 611*c*.

In the first greenhouse 1401, the first soil sensor 612*a* and the first discharge valve 609*a* are in a one-to-one relation. The first greenhouse 1401 allows one type of crop to be cultivated. Since there is only one unit of the soil sensor 612 in the first greenhouse 1401, it is impossible to cultivate two or more types of crops.

The second greenhouse 1402 has laid therein a second soil sensor 612*b*, the second discharge valve 609*b*, and a third discharge valve 609*c*.

The second discharge valve 609*b* has laid therein a fourth irrigation tube 611*d*, and a fifth irrigation tube 611*e*.

The third discharge valve 609*c* has laid therein a sixth irrigation tube 611*f* and a seventh irrigation tube 611*g*.

Therefore, when the second discharge valve 609*b* is opened with other discharge valves 609 closed, the culture solution being supplied from the water supply valve 604 and the culture stock solution supply valve 605 are sprayed on the soil in the second greenhouse 1402 by the fourth irrigation tube 611*d* and the fifth irrigation tube 611*e*.

Similarly, when the third discharge valve 609*c* is opened with other discharge valves 609 closed, the culture solution being supplied from the water supply valve 604 and the culture stock solution supply valve 605 are sprayed on the soil in the second greenhouse 1402 by the sixth irrigation tube 611*f* and the seventh irrigation tube 611*g*.

In the second greenhouse 1402, the second soil sensor 612*b*, the second discharge valve 609*b*, and the third discharge valve 609*c* are in a one-to-many relation. It is also impossible in the second greenhouse 1402 to cultivate two or more types of crops. In other words, the types of crops to be cultivated in a greenhouse are limited by the discharge valve 609 and the soil sensor 612.

The third greenhouse 1403 has laid therein a third soil sensor 612*c* and a fourth soil sensor 612*d*, and also a fourth discharge valve 609*d*.

The fourth discharge valve 609*d* has laid therein an eighth irrigation tube 611*h*, a ninth irrigation tube 611*i*, and a tenth irrigation tube 611*j*.

Therefore, when the fourth discharge valve 609*d* is opened with other discharge valves 609 closed, the culture solution being supplied from the water supply valve 604 and the culture stock solution supply valve 605 are sprayed on the soil in the third greenhouse 1403 by the eighth irrigation tube 611*h*, the ninth irrigation tube 611*i*, and the tenth irrigation tube 611*j*.

In the third greenhouse 1403, the third soil sensor 612*c*, the fourth soil sensor 612*d*, and the fourth discharge valve 609*d* are in a many-to-one relation. It is also impossible in the third greenhouse 1403 to cultivate two or more types of crops. In other words, the third soil sensor 612*c* and the fourth soil sensor 612*d* are laid not for cultivating a plurality of types of crops but for the purpose of improving the precision of the measurement value when cultivating a same type of crop.

Furthermore, the third greenhouse 1403 has installed therein the ventilation fan 613 and the boiler 614, as well as the air temperature sensor 615 for measuring air temperature in the third greenhouse 1403, as air conditioning equipment. The existence of the air conditioning equipment and the air temperature sensor 615 realizes air conditioning control of the greenhouse by the fertigation system 501. In order to realize the air conditioning control, there is needed a database for storing a relation between a greenhouse and a discharge valve, a relation between a greenhouse and air conditioning equipment, and a relation between a greenhouse and various sensors. The greenhouse number field of the discharge valve table 1303, the greenhouse table 1307, the air conditioning equipment table 1306, and the environment sensor table 1308 are provided for this purpose.

As thus described, one unit of the controller 505 has a plurality of the soil sensors 612 and one or more units of the discharge valve 609 associated therewith. In addition, the soil sensors 612 and the discharge valves 609 are in a many-to-many relation.

The relation between the soil sensors 612 and the discharge valves 609 can be identified from the discharge valve number field included in the soil sensor table 1302 and the soil sensor number field included in the discharge valve table 1303. In other words, a cultivable crop is identified by one or more units of the soil sensor 612 corresponding to one of units of the discharge valve 609. The amount and concentration of the culture solution to be supplied are then identified by one or more units of the discharge valve 609 corresponding to the soil sensor 612.

Further, the discharge valve 609 and the irrigation tubes 611 corresponding thereto are thus in a one-to-many relation.

As described above, the irrigation tube 611, which is a tube with one end closed by an end cap 802, has holes 801 opened at a regular interval for discharging culture solution or water.

Depending on the type of the irrigation tube 611, there is variation in the strength of culture solution supply, which is a culture solution supply amount per unit time. Therefore, the fertigation control server 510 according to the present embodiment records the types of the irrigation tubes 611 available from various makers and the strength of culture solution supply in the irrigation tube master 1305. Accordingly, the irrigation tube table 1304 has recorded therein the type and length of the irrigation tube 611 laid in a greenhouse of a farming family, and also which of the discharge valves 609 the irrigation tube 611 is connected to (whether or not being associated therewith).

The control data generating section 1006 of the fertigation control server 510 first calculates a culture solution supply amount per unit length of the irrigation tube 611 with regard to a crop associated with the discharge valve 609 specified from the controller 505. Next, the culture solution supply amount per unit length is multiplied by the full length of all of the irrigation tubes 611 associated with the discharge valve 609 to calculate the total amount of the culture solution to be supplied to the discharge valve 609. Next, dividing the total amount of the culture solution by the culture solution supply capacity per unit time of the discharge valve 609 makes it possible to calculate the opening time of the discharge valve 609, the water supply valve 604, and a culture solution supply valve 108.

Note that, when the quality of the irrigation tube 611 laid in the facilities of a farming family is high, the culture solution supply capacity of the irrigation tube 611 may be used instead of using the culture solution supply capacity per unit time of the discharge valve 609 for calculation of the opening time of the discharge valve 609, the water supply valve 604, and the culture solution supply valve 108.

In other words, the fertigation control server 510 according to the present embodiment is also a database system which appropriately grasps and manages the facilities of a greenhouse.

In the case of fertigation, unlike water cultivation, supplying culture solution in the soil does not immediately change the amount of water or EC. Therefore, simply registering the discharge valve 609 in a database does not allow for accurately calculating the culture solution supply amount to crops. The culture solution supply amount to a crop can only be accurately calculated by registering, in a database, the culture solution supply capacity of the discharge valve 609 together with all types and lengths of the irrigation tubes 611 connected to the discharge valve 609 in association therewith.

Note that a feedback control using the measurement value of the flow rate sensor 603 may be performed, instead of calculating the opening times of the discharge valve 609, the water supply valve 604, and the culture solution supply valve 108. In the above-described case, however, upon occurrence of any failure in the waterway introducing pressurized water, it is necessary for the fertigation control server 510 and/or the controller 505 to detect the occurrence and perform an appropriate exceptional process.

Returning to FIG. 13 again, description of the configuration of the device database 1009 will be continued.

The greenhouse table 1307 is a table of a greenhouse and has a device ID field and a greenhouse number field.

The device ID field is identical to the field bearing the same name in the first log table 1201.

The greenhouse number field stores a greenhouse number of a greenhouse belonging to (associated with) the controller 505 bearing the device ID.

The air conditioning equipment table 1306 is a table of an air conditioning equipment corresponding to a greenhouse, and has a device ID field, a greenhouse number field, an "air conditioning equipment ID" field, and a cooling/heating type field.

The device ID field is identical to the field bearing the same name in the first log table 1201.

The greenhouse number field is identical to the field bearing the same name in the greenhouse table 1307.

The "air conditioning equipment ID" field stores an air conditioning equipment ID for uniquely identifying air conditioning equipment installed in a greenhouse.

The cooling/heating type field stores type information indicating whether the air conditioning equipment identified by the air conditioning equipment ID is for cooling or heating.

The environment sensor table 1308 is a table of the air temperature sensor 615, a humidity sensor, or a solar radiation amount sensor corresponding to a greenhouse, and has a device ID field, a greenhouse number field, a sensor ID field, and a sensor type field.

The device ID field is identical to the field bearing the same name in the first log table 1201.

The greenhouse number field is identical to the field bearing the same name in the greenhouse table 1307.

The sensor ID field stores a sensor ID for uniquely identifying a sensor installed in a greenhouse.

The sensor type field stores type information indicating which of an air temperature sensor, a humidity sensor, or a solar radiation amount sensor the sensor identified by the sensor ID is.

[Operation of Controller 505]

Figure 15:
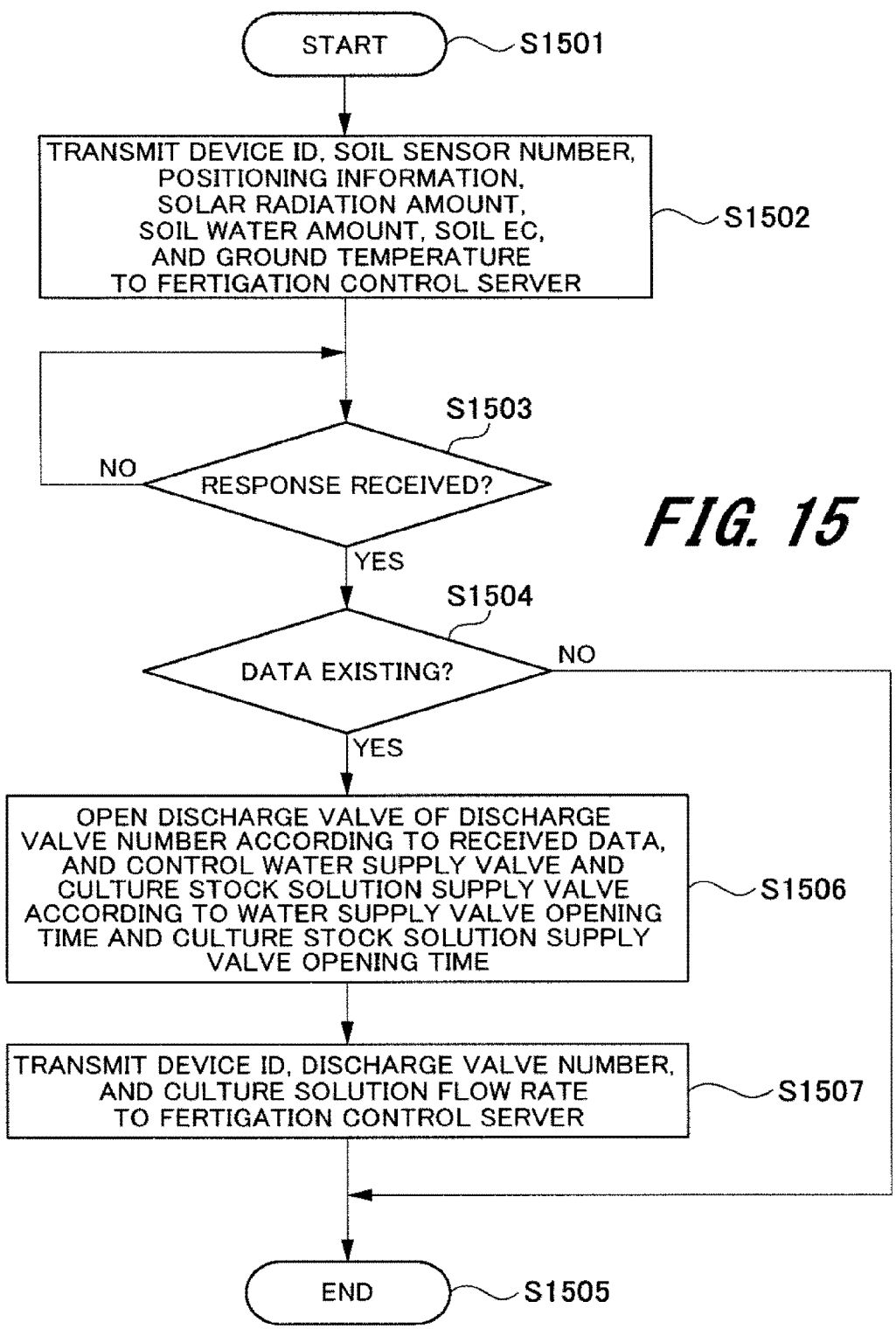
FIG. 15 is a flowchart illustrating an operation flow of a controller.

FIG. 15 is a flowchart illustrating an operation flow of the controller 505.

When the control section 804 of the controller 505 recognizes that a predetermined time has been reached and starts processing (S1501), the control section 804 first performs predetermined authentication with the fertigation control server 510 and subsequently activates the transmission information generating section 801. The transmission information generating section 801 converts the data of device ID, soil sensor number, positioning information, solar radiation amount, soil water amount, soil EC, ground temperature, or the like into XML text stream data. The control section 804 transmits the XML text stream data to the fertigation control server 510 via the web client 802 (S1502).

Next, the control section 804 waits until a response arrives from the fertigation control server 510 (NO at S1503).

Upon arrival of a response from the fertigation control server 510 (YES at S1503), the control section 804 next checks whether or not data of discharge valve number, water supply valve opening time, and culture stock solution supply valve opening time are included in the response (S1504). When the data is not included (NO at S1504), the series of processes is immediately terminated (S1505).

When, at step S1504, data of discharge valve number, water supply valve opening time, and culture stock solution supply valve opening time are included in the response received from the fertigation control server 510 (YES at S1504), the control section 804 activates the control signal generating section 803.

The control signal generating section 803 extracts a discharge valve number, a water supply valve opening time, and a culture stock solution supply valve opening time from the text stream data in the response received from the fertigation control server 510, and controls the water supply valve 604, the culture stock solution supply valve 605, and the discharge valve 609 (51506). Subsequently, upon completion of supply of culture solution to the target greenhouse, the control section 804 transmits the device ID, the discharge valve number, and the culture solution flow rate to the fertigation control server 510 via the web client 802 (S1507), and terminates the series of processes (S1505).

As can be seen in the processes of FIG. 15, the controller 505 only performs transmission of measurement values of various sensors to the fertigation control server 510, and an operation instructed from the fertigation control server 510. The controller 505 does not perform a process such as determining information by itself. Accordingly, the processing contents of the controller 505 are very simple.

Note that the processes illustrated in FIG. 15 are performed one by one on all of the discharge valves 609 connected to the controller 505. In the case of FIG. 14, the processes of FIG. 15 are performed on the first discharge valve 609a, the second discharge valve 609b, the third discharge valve 609c, and the fourth discharge valve 609d, respectively.

[Operation of Fertigation Control Server 510: Calculation Process of Culture Solution Amount and Concentration]

Figure 16:
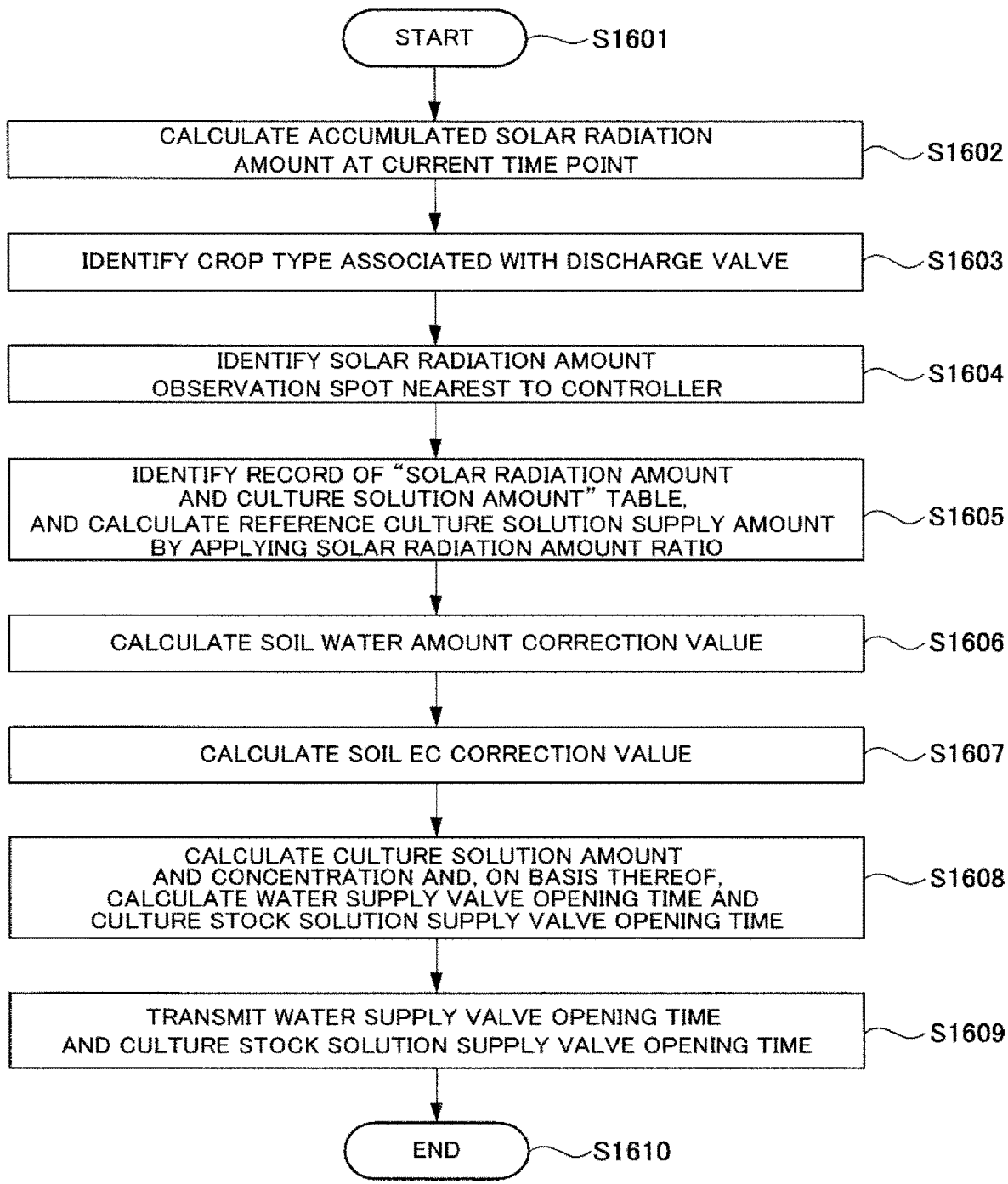
FIG. 16 is a flowchart illustrating a flow of a calculation process of culture solution amount and concentration for a discharge valve attached to a certain controller, performed by a control data generating section of a fertigation control server.

FIG. 16 is a flowchart illustrating a flow of a calculation process of culture solution amount and concentration, on a certain unit of the discharge valve 609 of a certain unit of the controller 505, performed by the control data generating section 1006 of the fertigation control server 510.

When the processing is started (S1601), the control data generating section 1006 first reads the value of the solar radiation amount field of the first log table 1201 using as a clue the device ID of the controller 505 received from the control section 1005, and calculates an accumulated solar radiation amount, over a period from the time point of calculating the previous culture solution amount or the like to the current time point, of the controller 505 currently accessing the fertigation control server 510 (S1602).

Next, the control data generating section 1006, referring to the discharge valve table 1303 and the soil sensor table 1302 using as a clue the device ID and the discharge valve number of the controller 505 received from the control section 1005, identifies the soil sensor 612 associated with the discharge valve 609, and further identifies the crop type associated with the soil sensor 612 (S1603).

Next, the control data generating section 1006 reads positioning information of the controller 505 from the first log table 1201. Subsequently, matching it with the positioning information table 1205, the control data generating section 1006 identifies the nearest observation spot of the solar radiation amount registered in the "solar radiation amount and culture solution amount" table 1204 (S1604).

Next, the control data generating section 1006 identifies a record of the "solar radiation amount and culture solution amount" table 1204 according to the identified positioning information, the date-and-time information acquired from the RTC 904, and the identified crop type. The control data generating section 1006 then compares the previously calculated accumulated solar radiation amount and the possible solar radiation amount stored in the identified record of the "solar radiation amount and culture solution amount" table 1204, and calculates a ratio of solar radiation amount. Subsequently, the control data generating section 1006 multiplies the calculated ratio of the solar radiation amount by the reference culture solution amount to calculate a reference culture solution supply amount for a certain unit of the discharge valve 609 at the current time point (S1605).

The control data generating section 1006, after having calculated the reference culture solution supply amount at step S1605, passes the calculated reference culture solution supply amount and various information required for referring to tables, such as the device ID, discharge valve number, or soil sensor number, of the controller 505 to the "culture solution amount fine adjustment" section 1102.

First, the "culture solution amount fine adjustment" section 1102 reads the soil water amount gradient in the soil on which the discharge valve 609 sprays culture solution, referring to the trend information table 1011 using as a clue the device ID and the discharge valve number. Next, the "culture solution amount fine adjustment" section 1102 reads the reference soil water amount in the soil on which the discharge valve 609 sprays culture solution and the soil water amount at the current time point, referring to the first log table 1201 using as a clue the device ID and the discharge valve number. Subsequently, the "culture solution amount fine adjustment" section 1102 calculates a correction value of the soil water amount, on the basis of the reference soil water amount, the soil water amount gradient, and the current soil water amount (S1606).

Next, the "culture solution amount fine adjustment" section 1102 reads the gradient of the soil EC value in the soil on which the discharge valve 609 sprays culture solution, referring to the trend information table 1011 using as a clue the device ID and the discharge valve number. The "culture solution amount fine adjustment" section 1102 then reads the reference soil EC in the soil to which the discharge valve 609 supplies culture solution and the soil EC at the current time point, referring to the first log table 1201 using as a clue the device ID and the discharge valve number. Subsequently, the "culture solution amount fine adjustment" section 1102 calculates a correction value of the soil EC on the basis of the reference soil EC, the gradient of the soil EC, and the current soil EC (S1607).

Next, the "culture solution amount fine adjustment" section 1102 adds the correction value of the soil water amount and the correction value of the soil EC to the reference culture solution supply amount to calculate final amount and concentration of the culture solution. Subsequently, the "culture solution amount fine adjustment" section 1102 calculates the opening time of the water supply valve 604 and the opening time of the culture stock solution supply valve 605, referring to the discharge valve table 1303, the irrigation tube table 1304, and the irrigation tube master 1305 (S1608).

Finally, the "culture solution amount fine adjustment" section 1102 transmits the opening time of the water supply valve 604 and the opening time of the culture stock solution supply valve 605 to the controller 505 via the web server program 1001 (S1609), and terminates the series of processes (S1610).

FIGS. 17A and 17B, and FIGS. 18A and 18B are schematic graphs illustrating a procedure of correcting the soil water amount by the "culture solution amount fine adjustment" section 1102. Note that the procedure of correcting the concentration of the culture solution on the basis of the reference soil EC is identical thereto, and therefore description of correcting the concentration of the culture solution will be omitted.

Figure 17A:
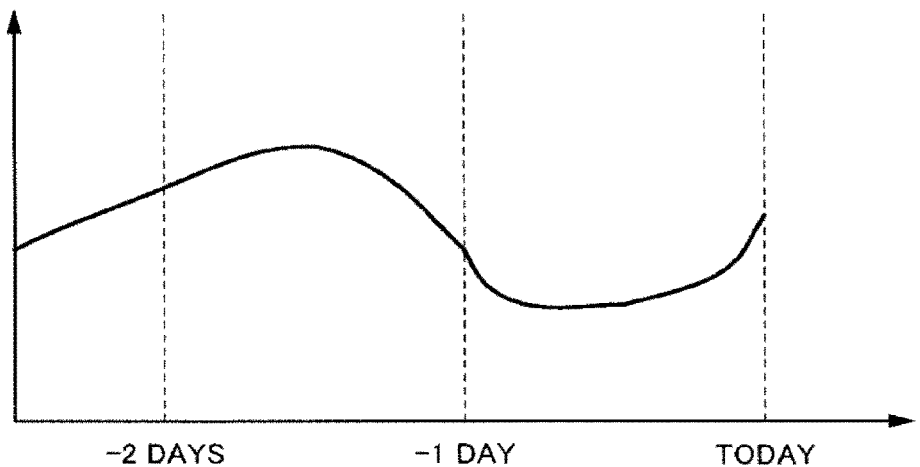
FIGS. 17A and 17B are schematic graphs illustrating a procedure of correcting the soil water amount by a culture solution amount fine adjustment section.

FIG. 17A is a graph illustrating an example of soil water amount for the immediately preceding two days. As illustrated in FIG. 17A, the soil water amount varies according to the weather, such as solar radiation amount, or the growth situation of crops.

Figure 17B:
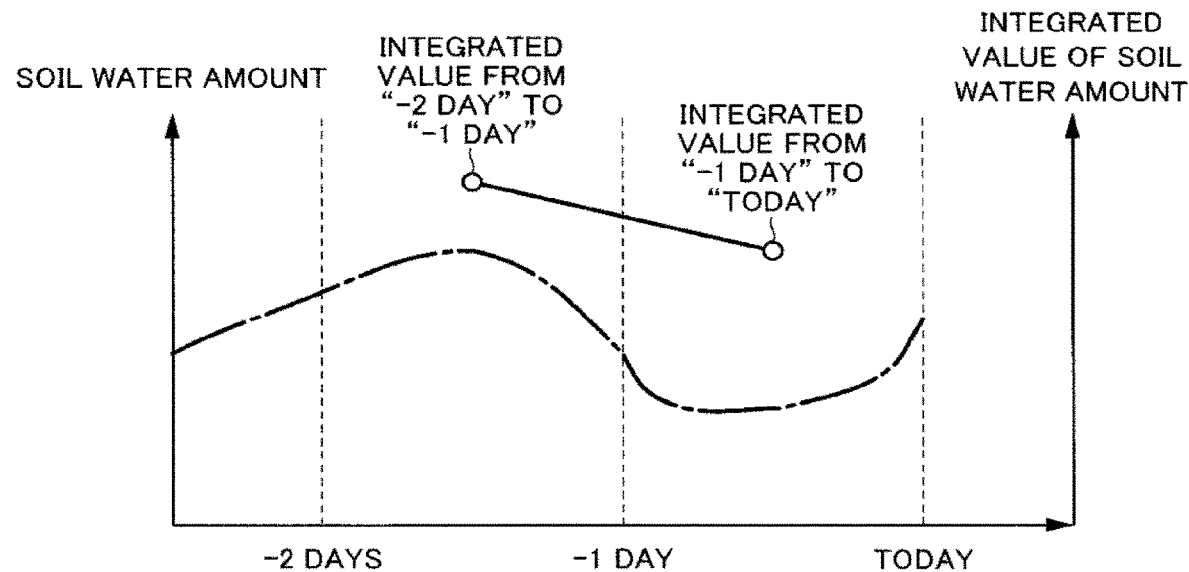

FIG. 17B is a graph illustrating an example of soil water amount for the immediately preceding two days and an integrated value thereof. As illustrated in FIG. 17B, an integrated value of soil water amount from "−2 day" to "−1 day", and an integrated value of soil water amount from "−1 day" to today are calculated in order to convert the variation of the soil water amount into a scalar value. Subsequently, the gradient is recorded in the trend information table 1011 as the soil water amount gradient.

Figure 18A:
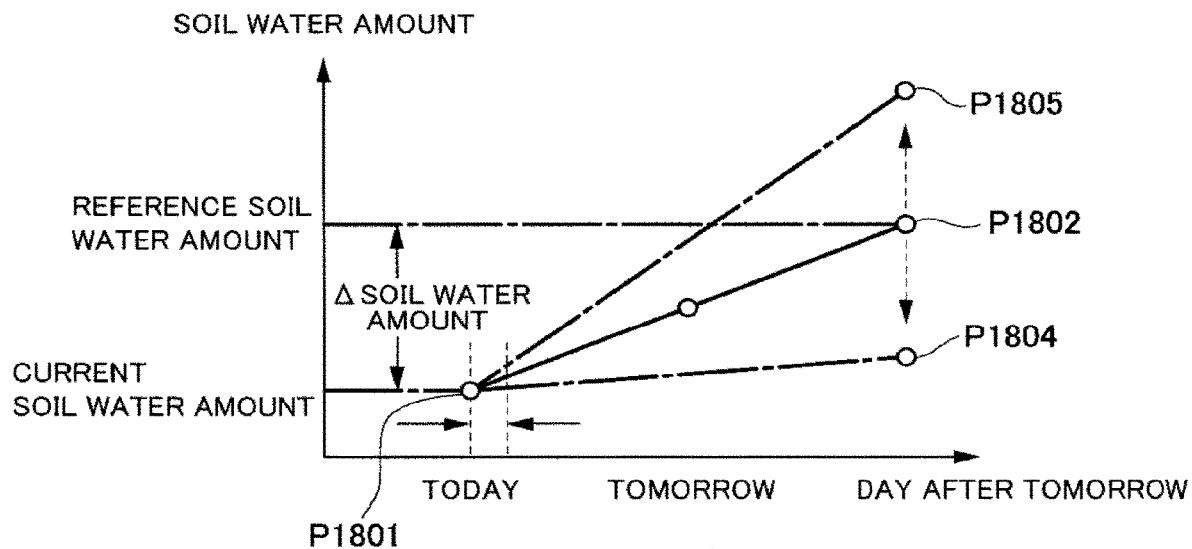
FIGS. 18A and 18B are schematic graphs illustrating a procedure of correcting the soil water amount by a culture solution amount fine adjustment section.

FIG. 18A is a schematic graph illustrating the difference between the current soil water amount and the reference soil water amount, and the trend-based correction.

Now, let us assume that the current soil water amount (point P1801) is insufficient relative to the reference soil water amount. The difference obtained by subtracting the current soil water amount from the reference soil water amount is denoted by Δ (soil water amount).

In the case of water cultivation, immediately correcting an insufficient or surplus amount of water causes the water amount to quickly follow. In the case of fertigation, however, suddenly increasing the amount of water by Δ (soil water amount) may result in over-supplying of water before water sufficiently seeps into the soil, leading to a state of excessive soil water amount. Therefore, the correction value of the water amount is determined with a thinking that correction of the soil water amount should take two days. In other words, water is replenished little by little so that the current soil water amount reaches the targeted reference soil water amount at the same time on the day after tomorrow (point P1802).

Figure 18B:
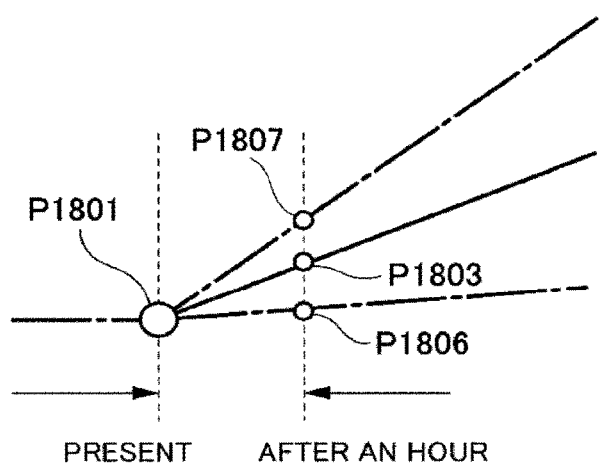

FIG. 18B is an enlarged view of a part of FIG. 18A. FIG. 18B is an explanatory view of a procedure of leading a target soil water amount from the current soil water amount.

Setting the timing of supplying the culture solution to once an hour, for example, results in supplying culture solution 13 times a day, given that the period from sunrise to sunset is from 6:00 in the morning to 18:00 in the evening. For a two-day span, a value obtained by dividing A (soil water amount) by 26 turns out to be the soil water amount to be corrected in one iteration (point P1803).

In addition, when correcting the soil water amount, it is necessary to consider how the soil water amount has been varying until then. Therefore, variation of the soil water amount up to two days before is preliminarily calculated as trend information. Then, when the soil water amount had increased, a correction is made so as to reduce the reference soil water amount. This is a trend-based minus correction (point P1804). When, on the contrary, the soil water amount had decreased, a correction is made so as to increase the reference soil water amount. This is a trend-based plus correction (point P1805).

According to the minus correction and the plus correction described above, the soil water amount to be corrected in one iteration also varies (points P1806 and P1807).

Up to today, there have been many approaches of calculation, as a way to automated crop cultivation using computer control, on the basis of the ratio, referred to as crop coefficients, of actual transpiration relative to water surface evaporation. Calculation of crop coefficients is advanced and complicated, and therefore not always adapted for transpiration of crops.

As is apparent from the description above, the fertigation system 501 of the present embodiment does not use any crop coefficients. Only a correction is made to follow the target soil water amount and the target soil EC after the reference culture solution amount has been calculated on the basis of positioning information, crop type, and solar radiation amount. The calculation can be essentially realized by the four basic arithmetic operations. Since the culture solution supply control performed by the fertigation control server 510 is a simple control, there is a very low risk of uncontrollability such as the amount or concentration of the culture solution becoming extremely insufficient or excessive. Depending on the type of crop, it is not impossible to cultivate and harvest the crop without monitoring the greenhouse at all, as long as the culture solution does not dry up.

[Change of Reference Soil Water Amount and Reference Soil EC Using Terminal]

Generally, a crop has its growth stages. The amount and concentration of culture solution required by a crop are different for each growth stage. Additionally, in the case of tomatoes, for example, increasing the culture solution amount results in an increased yield, whereas reducing the culture solution amount results in an improved taste and texture in exchange for a decreased yield.

Although the fertigation system 501 of the present embodiment supplies culture solution basically in a full automatic manner, it is possible to reflect an agriculture worker's know-how in the fertigation system 501 by changing the reference soil water amount and the reference soil EC by a person's manual operation.

Figure 19:
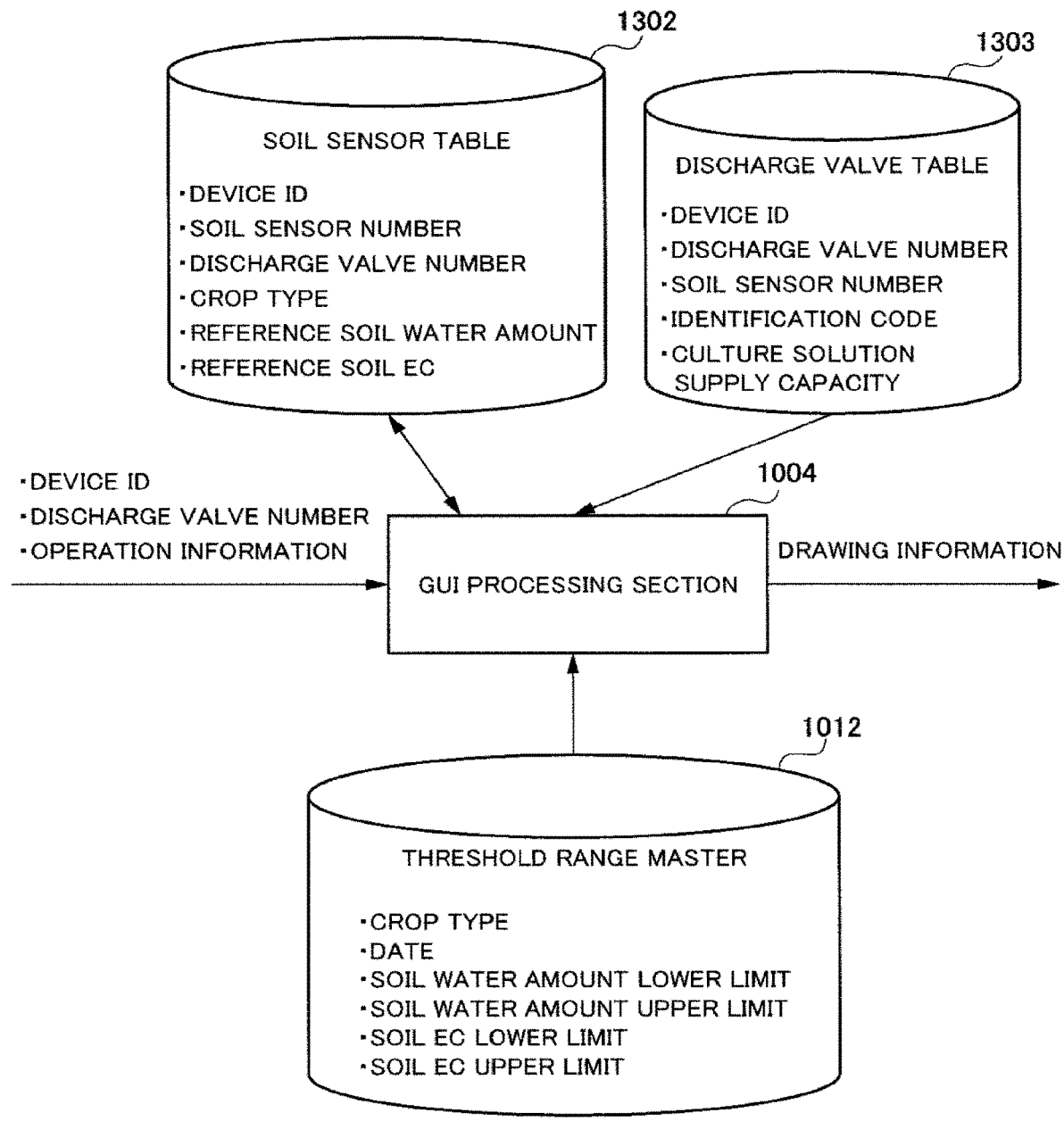
FIG. 19 is a block diagram illustrating processing contents of a GUI processing section.

FIG. 19 is a block diagram illustrating the processes performed by the GUI processing section 1004.

Figure 20A:
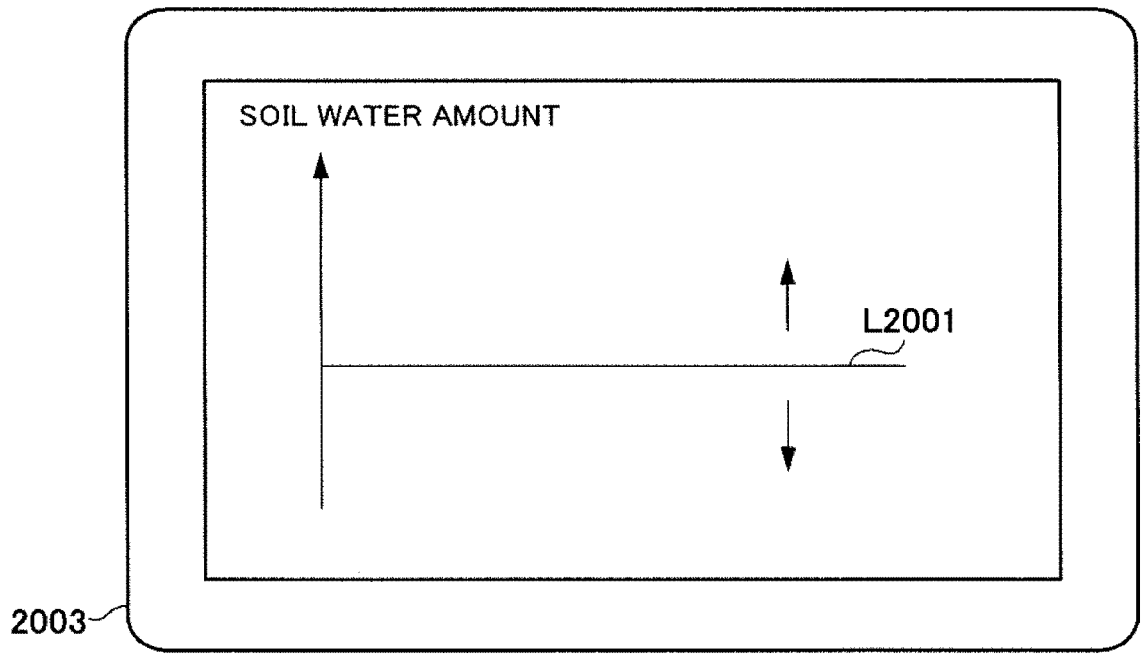
FIGS. 20A and 20B are operation screens displayed on a tablet terminal according to drawing information output by the GUI processing section.
Figure 20B:
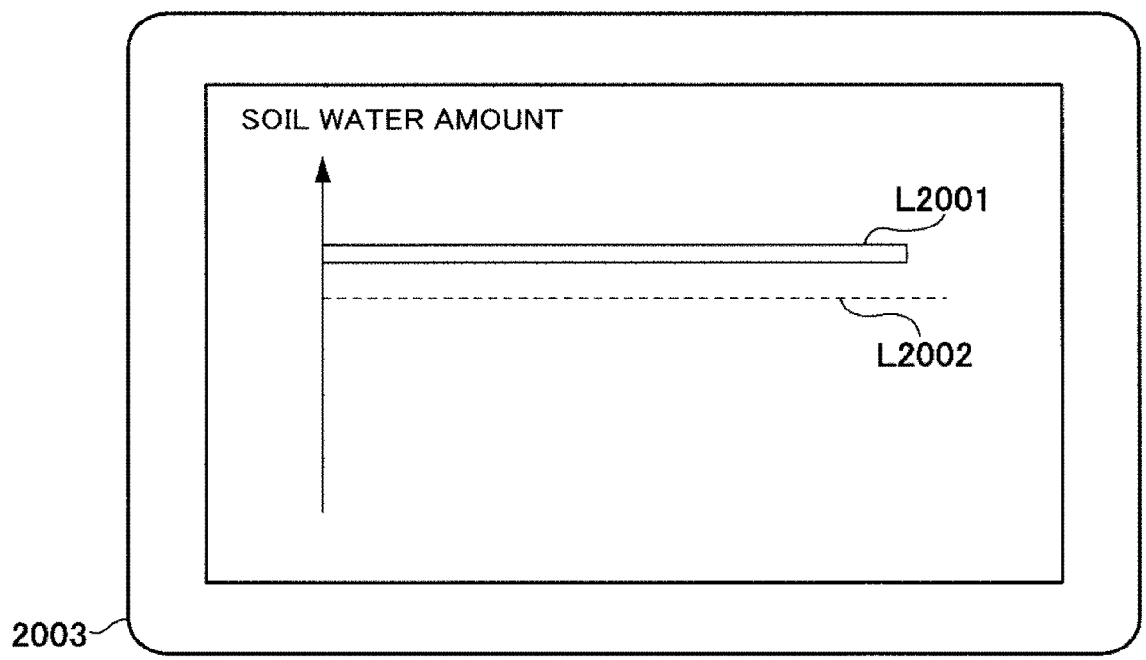

FIGS. 20A and 20B are operation screens displayed on a terminal 2003 in accordance with drawing information output from the GUI processing section 1004. Note that, hereinafter, each of the tablet terminal 507 and the smartphone 508 will be collectively referred to as the terminal 2003.

The GUI processing section 1004 displays an operation screen such as that illustrated in FIGS. 20A and 20B on the terminal 2003 operated by an agriculture worker. On this occasion, the GUI processing section 1004 receives a device ID and a discharge valve number from the control section 1005 and, referring to the discharge valve table 1303 and the soil sensor table 1302, outputs the reference soil water amount or the reference soil EC for a certain unit of the discharge valve 609, in a manner included in the drawing information.

As illustrated in FIG. 20A, the reference soil water amount is displayed on a crossbar L2001 in a graph-like operation screen displayed on the screen of the terminal 2003. The agriculture worker who is operating the terminal 2003 touches the crossbar L2001 displayed on the screen of the terminal 2003 to move it upward and downward. Accordingly, the reference soil water amount is changed in response to the amount which has been changed.

When, however, the reference soil water amount being set exceeds the soil water amount lower limit or the soil water amount upper limit registered in the threshold range master 1012 (L2002), the color of the crossbar L2001 is changed as an alarm function, as illustrated in FIG. 20B, to notify the operator that it is an abnormal value.

[Salts Accumulation Determination Function in Fertigation System]

In the foregoing, the fertigation system has been described, referring to FIGS. 5 to 20. The fertigation control server 510 of the fertigation system has provided therein the third log table 1203 for recording status information in the discharge valve 609 as information received from the terminal 2003, besides the first log table for recording measurement values of the soil sensor 612.

Although the above-mentioned second salts accumulation determination method is available regardless of whether or not a crop is being cultivated in the soil for which salts accumulation is to be determined, it is preferred that crops are not being cultivated when the determination is made. In a state where a crop is not being cultivated, nitrate ions in the soil will not be taken in the crops whereby a more correct determination becomes possible.

That is, in order to perform the second salts accumulation determination method in a state where a crop is not being cultivated, the fertigation control server 510 is required to grasp that a crop is not being cultivated in the soil for which salts accumulation is supposed to be determined from now in the fertigation system described above. Accordingly, the third log table 1203 for storing the status information indicating that a crop is not being cultivated is indispensable.

In addition, the terminal 2003 is indispensable for notifying the fertigation control server 510 that the glucose 201 aqueous solution or the reference culture solution 106 has been injected into the vicinity of the soil sensor.

FIGS. 21A, 21B, 21C, 22D, 22E, 22F, 23G, and 23H are display screens of the terminal 2003 for the salts accumulation determination function.

Hereinafter, the salts accumulation determination function, which is an additional function in the fertigation system, will be described. The salts accumulation determination function is implemented as an additional function in the GUI processing section 1004 of the fertigation control server 510.

The operation flow is as follows.

(1) First, the fertigation control server 510, upon receiving various pieces of information from the terminal 2003, records the pieces of information in the third log table 1203. On this occasion, presence or absence of crops being cultivated is checked for the discharge valves 609 associated with the controller 505 belonging to the terminal 2003. Then, when there is a partition bearing a discharge valve number in which cultivation is coming to an end, a screen for inquiring whether or not harvesting has been finished is displayed on the terminal 2003 (FIG. 21A). An operation button 2101 is displayed to a screen.

(2) When, there is no cultivation of crops for the discharge valve 609, a menu screen for selecting whether or not to perform determination of salts accumulation in the soil sensor 612 associated with the discharge valve 609 is presented on the terminal 2003 (FIG. 21B).

Figure 22D:
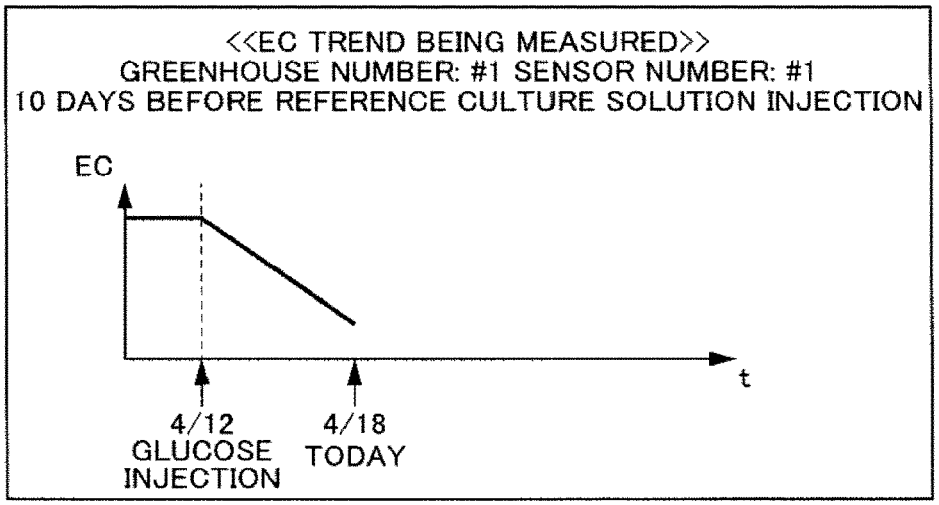
FIGS. 22D, 22E, and 22F are display screens of a terminal in accordance with a salts accumulation determination function.
Figure 23G:
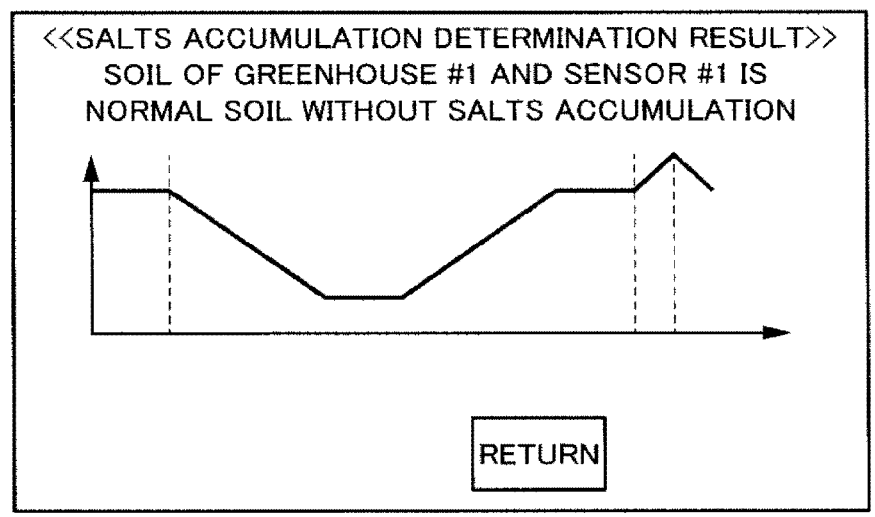
FIGS. 23G and 23H are display screens of a terminal in accordance with a salts accumulation determination function.

(3) Upon receiving an instruction to perform a determination process of salts accumulation from the terminal 2003, the GUI processing section 1004 records in the third log table 1203 status information indicating that an instruction of salts accumulation determination process has been received, and starts the salts accumulation determination process. The GUI processing section 1004 instructs injection of the glucose 201 to the agriculture worker via the terminal 2003 (FIG. 21C), continuously measures the EC value using the soil sensor 612, and keeps recording in the first log table. On this occasion, the GUI processing section 1004 displays the variation of the EC value on the terminal 2003 as a graph, upon receiving an inquiry from the terminal 2003 (FIG. 22D).

Figure 22E:
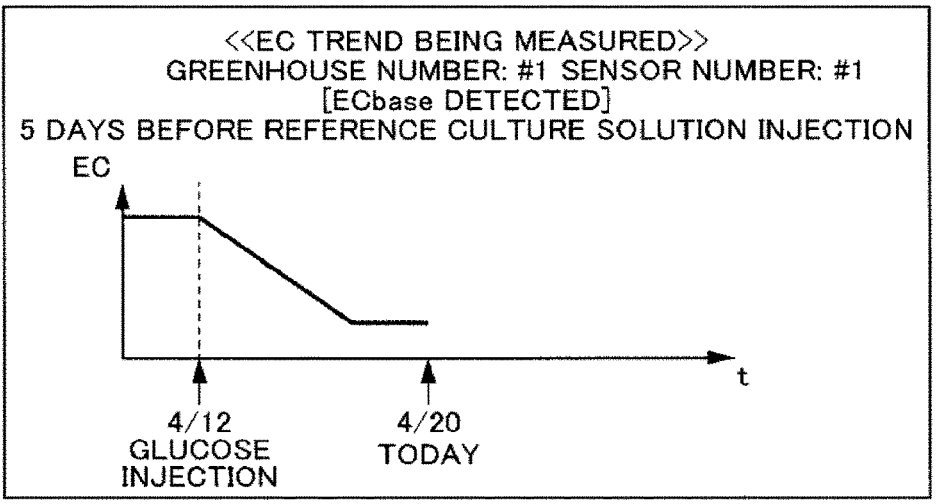

(4) Upon detecting ECbase from the EC value recorded in the first log table, the GUI processing section 1004 records ECbase in the third log table 1203 together with the status information. In addition, from this time point, the GUI processing section 1004 displays a message about detection of ECbase on the screen of the terminal 2003 when displaying the variation of the EC value as a graph upon receiving an inquiry from the terminal 2003 (FIG. 22E).

Figure 22F:
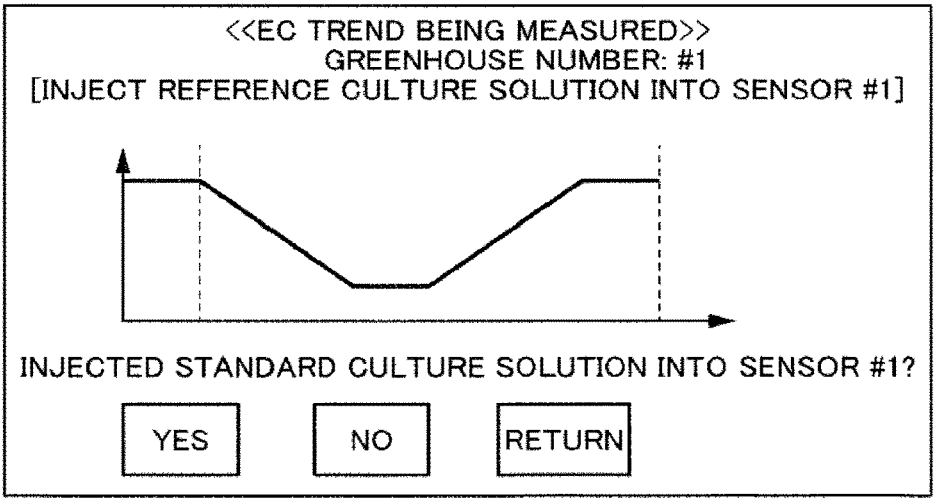

(5) When the EC value recorded in the first log table has risen from ECbase again, the GUI processing section 1004 instructs injection of reference culture solution to the agriculture worker via the terminal 2003 (FIG. 22F).

Figure 23H:
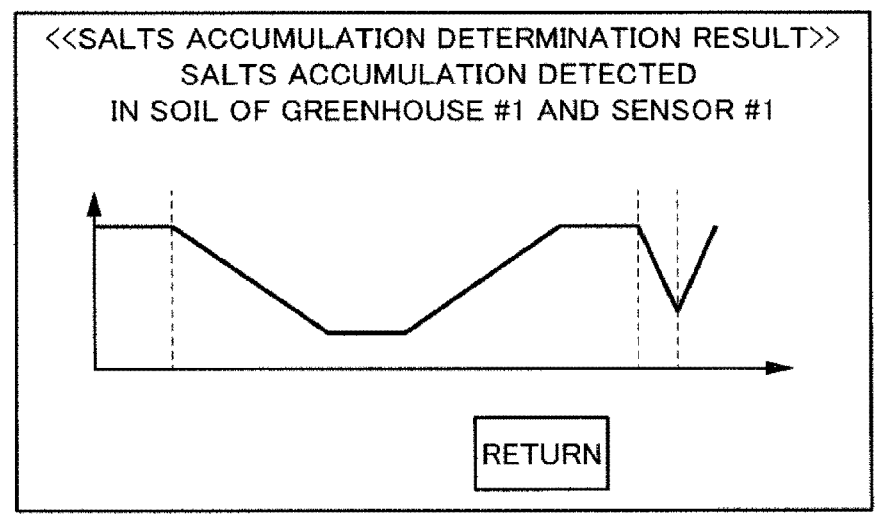

(6) The GUI processing section 1004 continues measurement of the EC value after the reference culture solution has been injected into the vicinity of the soil sensor and, when the EC value has finally reached an extreme value, performs a determination process of the salts accumulation of the soil. When the soil is determined to be normal, the GUI processing section 1004 displays a message notifying the fact on the terminal 2003 (FIG. 23G) and, when the soil is determined to have salts accumulated therein, displays a message notifying the fact on the terminal 2003 (FIG. 23H). Upon completion of the salts accumulation determination process, the GUI processing section 1004 records status information indicating that the salts accumulation determination process has been completed in the third log table 1203. Recording of status information is necessary, since it is impossible to cultivate crops in the partition associated with the soil sensor 612 performing the salts accumulation determination while the salts accumulation determination process is being performed.

Besides the above-described embodiments, applications such as those described below are conceivable.

(1) With regard to the irrigation tube 611, it is ideal to have all types of the irrigation tubes 611 circulating in the market registered in the irrigation tube master 1305. When, however, a new product is immediately introduced in a greenhouse, or an agriculture worker has originally created a type of the irrigation tube 611 by himself/herself, it turns out that there exists a type of the irrigation tube 611 which is not registered in the irrigation tube master 1305. In order to address such an exceptional situation, a "culture solution supply strength" field is provided in the irrigation tube table 1304. Then, water is poured into the irrigation tube 611 at the premise where the irrigation tube 611 is laid, and the culture solution supply strength of the irrigation tube 611 is directly measured and registered in the "culture solution supply strength" field of the irrigation tube table 1304. The irrigation tube type code has written therein information indicating that there is no registration of the irrigation tube 611 in the irrigation tube master 1305. Configuring the irrigation tube table 1304 in this manner also allows the fertigation control server 510 to handle an unregistered type of the irrigation tube 611 and calculate a correct water supply valve opening time and a correct culture stock solution supply valve opening time.

(2) Making use of weather forecast information as much as possible makes it possible to omit the solar radiation sensor 616 and calculate the reference culture solution supply amount only using a predicted amount of solar radiation.

(3) The solar radiation sensor 616 used in the fertigation system 501 of the present embodiment need not be of a very high precision. For example, various sensors are available such as those using small and inexpensive phototransistors, or the sensors may be replaced by solar panels.

(4) The fertigation system 501 illustrated in FIG. 21 is based on a specification such that a single type of culture stock solution provided by diluting high-concentration liquid fertilizer is further diluted with water to prepare culture solution. Depending on the type of crop, there may be a case which a single type of culture stock solution cannot handle. In order to handle such type of crop by the controller 505, it suffices to prepare a plurality of types of culture stock solution. In other words, a plurality of systems for preparing culture stock solution is provided in parallel. A culture stock solution supply valve is provided in each system.

For example, a first type of culture stock solution is applied to a first crop, and a second type of culture stock solution is applied to a second crop. The first type of culture stock solution is supplied from the first type of culture stock solution supply valve, whereas the second type of culture stock solution is supplied from the second culture stock solution supply valve. The plurality of culture stock solution supply valves which has been provided may be controlled exclusively in accordance with the type of crop via the controller 505, or, depending on the crops, the first type of culture stock solution and the second culture stock solution may be mixed. Configuring the fertigation system 501 in this manner allows the farming family to handle a wide variety of crops with a few facilities.

(5) As described above, the discharge valve 609 has a maximum tolerable flow rate. Since overloading the irrigation tube 611 connected to the discharge valve 609 may exceed the durability capacity of the discharge valve 609 and may damage the discharge valve 609, the length or the like of the irrigation tube 611 connectable to the discharge valves 609 is determined in accordance with the culture solution supply capacity of the irrigation tube 611 and the maximum tolerable flow rate of the discharge valves 609.

Accordingly, providing a discharge valve master for storing the type of discharge valve and information such as the maximum tolerable flow rate also for a discharge valve similarly to the irrigation tube master 1305 allows for providing the fertigation control server 510 with a facility layout planning support function when introducing the fertigation system 501 in a farming family. There are conceivable functions such as inputting a facility design chart from the terminal 2003, checking by the fertigation control server 510, displaying a warning on the terminal 2003 for a layout plan exceeding the maximum tolerable flow rate of the discharge valve 609, or the like.

(6) The fertigation system 501 of the present embodiment can be configured as a stand-alone system. In other words, integration of the controller and the fertigation control server results in a stand-alone fertigation system.

(7) The fertigation system 501 of the present embodiment can also have the following configuration.

<1> A fertigation system including:

a discharge valve configured to receive supply of culture solution from a culture solution preparing section that supplies the culture solution prepared by mixing water and culture stock solution, and control supply and interruption of the culture solution to soil in which a crop is cultivated;

a first irrigation tube configured to spray the culture solution on the soil, upon receiving supply of the culture solution from the discharge valve;

a second irrigation tube configured to spray the culture solution on the soil together with the first irrigation tube, upon receiving supply of the culture solution from the discharge valve;

a controller configured to control, on the basis of predetermined control information, preparation of the culture solution by the culture solution preparing section and opening and closing of the discharge valve; and a control data generating section configured to calculate an opening time of the discharge valve by the culture solution preparing section, on the basis of length of the first irrigation tube, length of the second irrigation tube, and culture solution supply capacity per unit time of the discharge valve, and provide the controller with the control information including the opening time of the discharge valve.

<2> The fertigation system according to <1>, further including:

a solar radiation sensor configured to measure strength of solar radiation;

a positioning information output section configured to output positioning information of a place where the crop is cultivated; and a "solar radiation amount and culture solution amount" table for recording a possible solar radiation amount and a reference culture solution amount corresponding to the possible solar radiation amount for each positioning information, type of crop, date, and time, wherein the control data generating section calculates a supply amount of the culture solution, taking into consideration the reference culture solution amount acquired by identifying a record of the "solar radiation amount and culture solution amount" table by the positioning information and a current date-and-time, and a solar radiation measurement value of the solar radiation sensor.

<3> The fertigation system according to <2>, further including;

a soil EC sensor configured to measure a soil EC value in the soil; and a sensor information table that stores a measurement value of the soil EC sensor, wherein the control data generating section calculates a supply amount of the culture solution, taking into consideration a trend of variation of the measurement value of the soil EC sensor from the sensor information table.

<4> The fertigation system according to <3>, further including:

a status information table that stores status information indicating whether or not a crop is being cultivated in the soil associated with the discharge valve, wherein the control data generating section checks that a crop is not being cultivated in the soil, and records a measurement value of the soil EC sensor for determination of salts accumulation in the sensor information table.

<5> A fertigation system including:

a first discharge valve configured to receive supply of culture solution from a culture solution preparing section that supplies the culture solution prepared by mixing water and culture stock solution, and control supply and interruption of the culture solution to a first soil area in which a crop is cultivated;

a first irrigation tube configured to spray the culture solution on the first soil area, upon receiving supply of the culture solution from the first discharge valve;

a second discharge valve configured to receive supply of the culture solution from the culture solution preparing section, and control supply and interruption of the culture solution to a second soil area which is different from the first soil area;

a second irrigation tube configured to spray the culture solution on the second soil area, upon receiving supply of the culture solution from the second discharge valve;

a controller configured to control, on the basis of predetermined control information, preparation of the culture solution by the culture solution preparing section and exclusive opening and closing of the first discharge valve and the second discharge valve; and a control data generating section configured to calculate an opening time of the first discharge valve by the culture solution preparing section, on the basis of culture solution supply capacity per unit time of the first discharge valve and length of the first irrigation tube, calculate an opening time of the second discharge valve by the culture solution preparing section, on the basis of culture solution supply capacity per unit time of the second discharge valve and length of the second irrigation tube, and provide the controller with first control information for control opening of the first discharge valve and second control information for control opening of the second discharge valve.

<6> The fertigation system according to <5>, further including:

a solar radiation sensor configured to measure strength of solar radiation;

a positioning information output section configured to output positioning information of a place where the crop is cultivated; and a "solar radiation amount and culture solution amount" table for recording a possible solar radiation amount and a reference culture solution amount corresponding to the possible solar radiation amount for each positioning information, type of crop, date, and time, wherein the control data generating section calculates a supply amount of the culture solution, taking into consideration the reference culture solution amount acquired by identifying a record of the "solar radiation amount and culture solution amount" table by the positioning information and a current date-and-time, and a solar radiation measurement value of the solar radiation sensor.

<7> The fertigation system according to <6>, further including;

a soil EC sensor configured to measure a soil EC value in the soil, wherein the control data generating section calculates a supply amount of the culture solution, taking into consideration a trend of variation of the measurement value of the soil EC sensor.

<8> The fertigation system according to <7>, further including:

a status information table that stores status information indicating whether or not a crop is being cultivated in the soil associated with the discharge valve, wherein the control data generating section checks that a crop is not being cultivated in the soil, and records a measurement value of the soil EC sensor for determination of salts accumulation in the sensor information table.

<9> A fertigation control server including:

a discharge valve table configured to store information of a discharge valve configured to receive supply of culture solution from a culture solution preparing section that supplies the culture solution prepared by mixing water and culture stock solution, and control supply and interruption of the culture solution to soil in which a crop is cultivated;

an irrigation tube table that stores information indicating relation with the discharge valve stored in the discharge valve table, culture solution supply capacity per unit length, and a length, of an irrigation tube configured to spray the culture solution on the soil, upon receiving supply of the culture solution from the discharge valve; and a control data generating section configured to calculate an amount of the culture solution to be supplied by the culture solution preparing section, on the basis of the culture solution supply capacity and lengths of all of the irrigation tubes registered in the irrigation tube table and associated with the discharge valve identified in the discharge valve table, and provide control information including the supply amount of the culture solution to a controller configured to control the culture solution preparing section and the discharge valve.

<10> The fertigation control server according to <9>, further including:

a sensor information table that stores a measurement value of a soil EC sensor connected to the controller and configured to measure a soil EC value of the soil associated with the discharge valve; and a status information table that stores status information indicating whether or not a crop is being cultivated in the soil associated with the discharge valve, wherein the control data generating section checks that a crop is not being cultivated in the soil from the status information table, and records, in the sensor information table, a measurement value of the soil EC sensor received from the controller for salts accumulation determination.

The salts accumulation determination method disclosed in the present embodiment injects glucose into the vicinity of an EC sensor in the soil for which it is desired to determine salts accumulation, and continuously measures the EC value. The EC value reaches a local minimum in the course of time. The EC value at this time point is acquired as ECbase. When the EC value rises again, reference culture solution is injected into the vicinity of the EC sensor. It is checked that, in the course of time, the rise or drop of the EC value has reached an extreme value and returned to its original value from the EC value at the time point of injecting the reference culture solution. Subsequently, a value acquired by subtracting the EC value at the time point of injecting the reference culture solution from the EC value at the time point of reaching the extreme value is compared with ECbase to determine salts accumulation. Although it requires a relatively long period, presence of absence of salts accumulation in the soil can be determined simply and precisely.

The fertigation system 501 disclosed in the present embodiment includes the controller 505 which transmits sensor data to the fertigation control server 510 and controls the water supply valve 604, the culture stock solution supply valve 605, and the discharge valve 609 on the basis of the received data, and the fertigation control server 510 which calculates control amounts for the water supply valve 604, the culture stock solution supply valve 605, and the discharge valve 609 on the basis of the sensor data received from the controller 505, and returns the control amounts to the controller 505.

First, the fertigation system 501 of the present embodiment is capable of cultivating a plurality of types of crops, or crops with shifted planting times in a single facility, using a combination of the water supply valve 604, the culture stock solution supply valve 605, and the discharge valve 609.

Second, the fertigation system 501 of the present embodiment is capable of accurately grasping the culture solution spray amount per unit time of the irrigation tube 611, by registering, in the fertigation control server 510, the type and length of the irrigation tube 611 connected to the discharge valve 609. Accordingly, it is possible to calculate accurate control amounts for the water supply valve 604, the culture stock solution supply valve 605, and the discharge valve 609.

Third, the fertigation system 501 of the present embodiment, is capable of calculating, although the calculation process being simple and low-load, control amounts for the water supply valve 604, the culture stock solution supply valve 605, and the discharge valve 609 which can be flexibly and appropriately adapted to the growth situation of crops, by determining a reference culture solution supply amount in a manner following the solar radiation, and subsequently adding a control that follows the reference soil water amount and the reference soil EC.

Fourth, the fertigation system 501 of the present embodiment allows for introducing the know-how of agriculture workers in a machine-control system without difficulties, and preventing excessive or insufficient supply of culture solution, by allowing the agriculture workers to arbitrarily change the reference soil water amount and the reference soil EC.

Fifth, the fertigation system 501 of the present embodiment is capable of accurately determining salts accumulation as an additional function, by grasping facilities and the status thereof in a farming family.

Although embodiments of the present invention have been described above, the present invention is not limited to the above-described embodiments, and other variations or applications are included therein as long as they do not deviate from the scope of the present invention described in the claims.

For example, the above-described embodiments explain the components of devices and systems in detail and specifically for the purpose of explaining the present invention in a comprehensible manner, and therefore are not limited to those including all of the above-described components. In addition, it is possible to replace some of the components of a certain embodiment by components of another embodiment and, furthermore, it is also possible to add a component of another embodiment to components of a certain embodiment. In addition, a part of the components of respective embodiments can be added to, deleted from, or replace other components.

In addition, a part or all of the above-described components, functions, processing sections or the like may be implemented by hardware such as those designed as integrated circuits, for example. In addition, the above-described components, functions or the like may be implemented by software including programs that may be interpreted and executed by processor to realize respective functions. Information such as programs, tables, files, or the like, for realizing respective functions can be held in a volatile or nonvolatile storage such as a memory, a hard disk, or an SSD (Solid State Drive), or in a storage medium such as an IC card, an optical disk, or the like.

In addition, control lines or information lines are illustrated where considered necessary for explanation, and not all the control lines or information lines are necessarily illustrated in a product. Actually, it may be considered that almost all the components are connected to each other.

REFERENCE SIGNS LIST

101: soil, 102: EC sensor, 103: data logger, 104: tube, 105: syringe, 106: reference culture solution, 108: culture solution supply valve, 201: glucose, 401: EC sensor, 402: porous cup, 403: electrode, 405: coaxial cable, 406: core line, 407: pipe, 408: cap, 411: simplified EC value measurement device, 415: square wave voltage source, 417: comparator, 418: EXOR gate, 419: LPF, 420: control section, 501: fertigation system, 502: greenhouse, 503: vinyl house, 504: agriculture worker, 505: controller, 506: agriculture worker, 507: tablet terminals, 508: smartphone, 509: Internet, 510: fertigation control server, 511: weather forecast server, 601: liquid fertilizer tank, 602: liquid fertilizer mixer, 603: flow rate sensor, 604: water supply valve, 605: culture stock solution supply valve, 606: culture solution preparing section, 607: greenhouse, 608: first partition, 609: discharge valve, 610: second partition, 611: irrigation tube, 612: soil sensor, 613: ventilation fan, 614: boiler, 615: air temperature sensor, 616: solar radiation sensor, 617: GPS terminal, 618: wireless communication section, 701: culture stock solution supply valve, 702: second culture stock solution supply valve, 801: hole, 802: end cap, 701: CPU, 702: ROM, 703: RAM, 704: RTC, 705: NIC, 706: first serial interface, 707: bus, 708: A/D converter, 709: multiplexer, 910: second serial interface, 801: transmission information generating section, 802: web client, 803: control signal generating section, 804: control section, 805: authentication information, 901: CPU, 902: ROM, 903: RAM, 904: RTC, 905: NIC, 906: nonvolatile storage, 907: bus, 908: display section, 909: operation section, 1001: web server program, 1002: authentication processing section, 1003: received-data processing section, 1004: GUI processing section, 1005: control section, 1006: control data generating section, 1007: user master, 1008: log database, 1009: device database, 1010: solar radiation amount database, 1011: trend information table, 1012: threshold range master, 1013: trend information calculating section, 1101: reference culture solution amount calculating section, 1102: culture solution amount fine adjustment section, 1201: first log table, 1202: second log table, 1203: third log table, 1204: "solar radiation amount and culture solution amount" table, 1205: positioning information table, 1301: device master, 1302: soil sensor table, 1303: discharge valve table, 1304: irrigation tube table, 1305: irrigation tube master, 1306: air conditioning equipment table, 1307: greenhouse table, 1308: environment sensor table, 1401: first greenhouse, 1402: second greenhouse, 1403: third greenhouse, 2003: terminal, 2101: operation button

The invention claimed is:

1. A fertigation system comprising:
a first discharge valve configured to receive and control a first supply of culture solution that includes water and culture stock solution, from a culture solution preparing section that supplies the culture solution, to a first soil area where a crop is cultivated;
a first irrigation tube configured to spray the culture solution on the first soil area, upon receiving the first supply of the culture solution from the first discharge valve;
a second discharge valve configured to receive and control a second supply of the culture solution from the culture solution preparing section, to a second soil area where a crop is cultivated;
a second irrigation tube configured to spray the culture solution on the second soil area, upon receiving the second supply of the culture solution from the second discharge valve;
a first soil EC sensor configured to measure a soil EC value in the first soil area to which the first supply of the culture solution is sprayed;
a second soil EC sensor configured to measure a soil EC value in the second soil area to which the second supply of the culture solution is sprayed;
a sensor information table that stores measurement values of the first soil EC sensor and the second soil EC sensor,
a controller configured to control, on a basis of predetermined control information, exclusive opening and closing of the first discharge valve and the second discharge valve; and
a control data generating section configured to i) calculate a first supply amount of the culture solution to be supplied to the first irrigation tube, on a basis of culture solution supply capacity per unit length of the first irrigation tube and length of the first irrigation tube, and provide the controller with first control information to control the opening and closing of the first discharge valve based upon the first supply amount of the culture solution to be supplied to the first irrigation tube, and ii) calculate a second supply amount of the culture solution to be supplied to the second irrigation tube, on a basis of culture solution supply capacity per unit length of the second irrigation tube and length of the second irrigation tube, and provide the controller with second control information to control opening and closing of the second discharge valve based upon the second supply amount of the culture solution to be supplied to the second irrigation tube,
wherein the control data generating section calculates the first supply amount of the culture solution to be supplied to the first irrigation tube and the second supply amount of the culture solution to be supplied to the second irrigation tube, based on a trend of variation of the measurement values of the first soil EC sensor and the second soil EC sensor, stored in the sensor information table.

2. The fertigation system according to claim 1, wherein the control data generating section i) calculates, as the first control information for controlling opening and closing of the first discharge valve, a first opening time of the first discharge valve that is necessary for supplying the first supply amount of the culture solution to the first irrigation tube, and provides the controller with the first control information including the first opening time of the first discharge valve, and ii) calculates, as the second control information for controlling opening and closing of the second discharge valve, a second opening time of the second discharge valve that is necessary for supplying the second supply amount of the culture solution to the second irrigation tube, and provides the controller with the second control information including the second opening time of the second discharge valve.

3. The fertigation system according to claim 2, further comprising:
a solar radiation sensor configured to measure strength of solar radiation in at least one of the first soil area and the second soil area;
a positioning information output section configured to output positioning information of at least one of the first soil area and the second soil area; and a solar radiation amount and culture solution amount table for recording a solar radiation amount and a reference culture solution amount corresponding to the solar radiation amount, for each of positioning information, type of crop, date, and time, wherein the control data generating section calculates the first supply amount of the culture solution to be supplied to the first irrigation tube and the second supply amount of the culture solution to be supplied to the second irrigation tube, taking into consideration i) the reference culture solution amount, acquired by identifying a record of the solar radiation amount and culture solution amount table with the positioning information of the at least one of the first soil area and the second soil area, output by the positioning information output section, and a current date-and-time, and ii) a solar radiation measurement value of the solar radiation sensor at the current date-and-time.

4. The fertigation system according to claim 3, further comprising:

a status information table that stores status information indicating whether or not a crop is being cultivated in the first soil area associated with the first discharge valve and in the second soil area associated with the second discharge valve, wherein the control data generating section checks that a crop is not being cultivated in at least one of the first soil area and the second soil area, and records the measurement values of the first soil EC sensor and the second soil EC sensor in the sensor information table, for determination of salts accumulation.

5. A fertigation control server comprising:

a discharge valve table that stores information related to discharge valves each configured to receive supply of a culture solution prepared by mixing water and culture stock solution, from a culture solution preparing section that supplies the culture solution, and control supply and interruption of the culture solution to soil where a crop is cultivated;

an irrigation tube table that stores information indicating relation with the discharge valves stored in the discharge valve table, culture solution supply capacities per unit length, and lengths of irrigation tubes each configured to spray the culture solution on the soil, upon receiving supply of the culture solution from an associated discharge valve of the discharge valves;

a sensor information table that stores a measurement value of a soil EC sensor connected to a controller and configured to measure a soil EC value of the soil associated with the discharge valve to which the culture solution is sprayed;

a status information table that stores status information indicating whether or not a crop is being cultivated in the soil associated with the discharge valve; and a control data generating section configured to calculate a supply amount of the culture solution to be supplied by the culture solution preparing section, on a basis of the culture solution supply capacities and lengths that are read out from the irrigation tube table, of all of the irrigation tubes associated with discharge valves identified in the discharge valve table, and provide control information for controlling opening and closing of the discharge valves based on the supply amount of the culture solution to be supplied by the culture solution preparing section, to the controller configured to control the culture solution preparing section and the discharge valves, wherein the control data generating section checks that a crop is not being cultivated in the soil from the status information table, and records a measurement value of the soil EC sensor received from the controller in the sensor information table, for salts accumulation determination.

6. The fertigation control server according to claim 5, wherein the control data generating section calculates, as the control information for controlling opening and closing of the discharge valve, an opening time of the discharge valve that is necessary for supplying the culture solution, and provide the controller with the control information including the opening time of the discharge valve.

* * * * *